US009795953B2

(12) United States Patent
Jensen et al.

(10) Patent No.: US 9,795,953 B2
(45) Date of Patent: Oct. 24, 2017

(54) ORGANOMETALLIC CATALYSTS

(71) Applicant: Bergen Teknologioverforing AS, Bergen (NO)

(72) Inventors: Vidar R. Jensen, Bergen (NO); Giovanni Occhipinti, Kleppesto (NO)

(73) Assignee: Bergen Teknologioverforing AS, Bergen (NO)

( * ) Notice: Subject to any disclaimer, the term of this patent is extended or adjusted under 35 U.S.C. 154(b) by 0 days.

(21) Appl. No.: 15/087,413

(22) Filed: Mar. 31, 2016

(65) Prior Publication Data
US 2016/0214098 A1 Jul. 28, 2016

Related U.S. Application Data

(63) Continuation of application No. 14/334,302, filed on Jul. 17, 2014, now Pat. No. 9,303,100.

(60) Provisional application No. 61/847,251, filed on Jul. 17, 2013.

(51) Int. Cl.
*C07C 2/02* (2006.01)
*C07C 2/32* (2006.01)
*C07C 2/34* (2006.01)
*C07F 15/00* (2006.01)
*B01J 31/22* (2006.01)
*C08F 4/80* (2006.01)
*C07C 6/04* (2006.01)
*C07C 67/475* (2006.01)
*C07F 7/08* (2006.01)

(52) U.S. Cl.
CPC ............ *B01J 31/2278* (2013.01); *C07C 2/02* (2013.01); *C07C 2/32* (2013.01); *C07C 2/34* (2013.01); *C07C 6/04* (2013.01); *C07C 67/475* (2013.01); *C07F 7/083* (2013.01); *C07F 15/002* (2013.01); *C07F 15/0046* (2013.01); *C08F 4/80* (2013.01); *B01J 2231/543* (2013.01); *B01J 2531/821* (2013.01); *C07C 2531/22* (2013.01)

(58) Field of Classification Search
CPC ..... C07C 2/02; C07C 2/32; C07C 2/34; C07F 15/0046; C07F 15/002; B01J 31/22
See application file for complete search history.

(56) References Cited

U.S. PATENT DOCUMENTS 9,303,100 B2  4/2016  Jensen et al.

FOREIGN PATENT DOCUMENTS

EP       2826783 A1      1/2015
WO    WO 2012/032131  *  3/2012

OTHER PUBLICATIONS

Extended European Search Report and European Search Opinion mailed Dec. 18, 2014 in connection with EP14177478.6.
Occhipintietal et al., Theory-assisted development of a robust and Z-selective olefin metathesis catalyst. Dalton Trans. Aug. 7, 2014;43(29):11106-17. doi: 10.1039/c4dt00409d. Epub Apr. 30, 2014.
Tanaka et al., Anionic Ligand Exchange in Hoveyda-Grubbs Ruthenium(II) Benzylidenes. Organometallics, 2006, 25 (24), pp. 5696-5698. doi: 10.1021/om060913n. Epub Oct. 18, 2016.
Torker et al., The influence of anionic ligands on stereoisomerism of Ru carbenes and their importance to efficiency and selectivity of catalytic olefin metathesis reactions. J Am Chem Soc. Mar. 5, 2014;136(9):3439-55. doi: 10.1021/ja410606b. Epub Feb. 17, 2014.

* cited by examiner

*Primary Examiner* — Caixia Lu
(74) *Attorney, Agent, or Firm* — Wolf, Greenfield & Sacks, P.C.

(57) ABSTRACT

The present invention refers to novel ruthenium- and osmium-based catalysts for olefin metathesis reactions, particularly to catalysts having stereoselective properties. Z-selectivity is obtained by utilizing two mono-anionic ligands of very different steric requirement. In olefin metathesis reactions these catalysts selectively provide the Z-isomer of disubstituted olefinic products even in presence of air or of acids.

18 Claims, 2 Drawing Sheets

ORGANOMETALLIC CATALYSTS

CROSS REFERENCE TO RELATED APPLICATION(S)

This application is a Continuation application of U.S. application Ser. No. 14/334,302, filed Jul. 17, 2014, now U.S. Pat. No. 9,303,100, issued Apr. 5, 2016, which claims the benefit of and priority to U.S. Provisional Patent Application No. 61/847,251, filed Jul. 17, 2013, the entire contents of which is incorporated herein by reference in its entirety.

DESCRIPTION

The present invention refers to novel catalysts for olefin metathesis reactions, particularly to catalysts capable of predominantly giving the Z-isomers of olefinic products.

BACKGROUND OF THE INVENTION

Catalysed olefin metathesis is one of the most flexible ways in which to make carbon-carbon bonds in general and double bonds (C=C) in particular (1, 2, 3). This reaction formally cleaves two different carbon-carbon double bonds (C=C) into four fragments that are recombined with two new C=C double bonds to form olefinic products in which the original fragment partners are exchanged. The last 10 years have seen an almost explosive increase in the use of this reaction for the production of fine chemicals, polymers and pharmaceuticals. The reaction is catalysed and the market for metathesis catalysts is reportedly worth $1.5 bn (12.5% of the total worldwide market for catalysts) and is expanding by 9-10% annually. The product of this transformation is in general a mixture of cis (Z) and trans (E) disubstituted isomers, with the thermodynamically more stable E-isomer usually being the major component. However, in certain instances the target product is either the pure E- or the pure Z-isomer.

For example, the biological, chemical and physical properties within a given pair of E- and Z-isomers may, in fact, be very different, highlighting the need for selective production of single isomers. The isomer mixtures produced have to be subjected to costly separation processes. Sometimes, the separation may be very challenging (4).

The catalyst is the main key to controlling the ratio with which the isomers are formed and the availability of robust and industrially compatible stereoselective catalysts is expected to expand the applicability of olefin metathesis in organic synthesis and polymerisation chemistry (3). Such catalysts would have a particular impact on the synthesis of large macrocycles by ring closing metathesis (RCM), stereoregular polymers (ROMP), and stereoisomeric pure alkenes. The Z-alkene functionality is, in fact, required in many cases, either because it is present in the target molecule or because it is necessary for subsequent stereospecific transformations. A range of natural products with biological activity (e.g. anticancer, antibacterial, and antifungal) contain Z-alkene macrocyclic frameworks, see Table 1. In most of the cases, the cost of extraction of these molecules is prohibitive, and total synthesis is the only alternative (4, 5). The formation of such large rings is very challenging, with RCM standing out among the few alternative routes (1, 5, 6).

TABLE 1

Representative examples of natural products to which synthetic access could be drastically simplified via cis-selective olefin metathesis.

| Natural product | Properties and application |
| --- | --- |
| Nakadomarine A | Anticancer, antifungal and antibacterial |
| Epothilone A ($) | Potent anticancer |
| Epothilone C ($) | Potent anticancer |
| Turrianes | Antineoplastic agents |
| Motuporamine C | Cytotoxic activity and/or anti-metaplastic activity. Robust inhibitor of chick neurite outgrowth |
| Cruentaren A | Highly cytotoxic F-ATPase inhibitor |
| Latrunculin A ($) | Actin-binding |
| Latrunculin B ($) | Highly selective actin-binding |
| Sophorolipid lactone | Microbial biosurfactant |
| Epilachnene ($) | Antiinsectan activity |
| Civetone ($) | Musk odor for perfumes |
| Yuzu lactone | Olfactory molecule |
| Ambretolide | Olfactory molecule |

($): commercial products

The stereochemical outcome is in general unpredictable and depends on many factors such as the nature of the substrate and of the catalyst, the reaction conditions and on the presence of specific additives (7-10). Time consuming and very costly empirical approaches are therefore required to improve the process of manufacturing the individual molecules. Hence, the quest for efficient stereoselective catalysts is to a large extent driven by commercial needs (3).

In recent years, several highly Z-selective catalysts have been discovered. The first examples were disclosed by Schrock and Hoveyda (cf., for example, catalyst A, FIG. 2) (11-14). These catalysts are based on molybdenum or tungsten and are capable of promoting metathesis transformations such as ring opening/cross metathesis (ROCM) (12), ring opening metathesis polymerisation (ROMP) (13), olefin homocoupling (14), cross-metathesis (CM) (15, 16), and RCM (17, 18).

More recently highly Z-selective ruthenium-based catalysts have been discovered. Grubbs and co-workers have developed Ru-catalysts involving a bidentate N-heterocyclic carbene (NHC)-adamantyl ligand. These catalysts have shown high selectivity in several processes: cross-metathesis (CM) (19), olefin homocoupling (20, 21), ring opening metathesis polymerisation (ROMP) (22, 23), ring closing metathesis (RCM) (24, 25), and ring opening/cross-metathesis (ROCM) (26). A different system, containing one 2,4,6-triphenylbenzenethiolate ligand has so far demonstrated high Z-selectivity in homocoupling reactions (27, 28). Finally, very recently Hoveyda and coworkers have developed another highly Z-selective system containing a dithiolate ligand (29), which has been applied in ring opening metathesis polymerisation (ROMP) and ring-opening/cross-metathesis (ROCM).

However, none of the Z-selective catalysts reported to date (i.e., neither those based on molybdenum or tungsten, nor those based on ruthenium) have demonstrated tolerance towards presence of air or acids during catalysis.

The present invention addresses the need for active and functional group tolerant stereoselective olefin metathesis catalysts by utilising anionic ligands of very different steric requirement. In olefin metathesis reactions, the thus obtained ruthenium and osmium catalysts selectively provide the thermodynamically less favoured Z-isomers. In addition to being Z-stereoselective, these catalysts display many of the attractive properties of commonly employed (i.e., non Z-selective) ruthenium-based catalysts for olefin metathesis. In particular, embodiments of the invention are highly active catalysts and demonstrate superior stability in air and under protic conditions. For example, in contrast to the other Z-selective catalysts, the systems of the present invention are able to affect Z-selective olefin metathesis in air using non-degassed (i.e., stored under air) olefinic substrates and solvents. Z-selective olefin metathesis can be carried out also in presence of a relatively strong acid (e.g. phenylphophoric acid, one equivalent relative to catalyst). Moreover, they show tolerance towards a range of functional groups and solvents.

SUMMARY OF THE INVENTION

Figure 1:
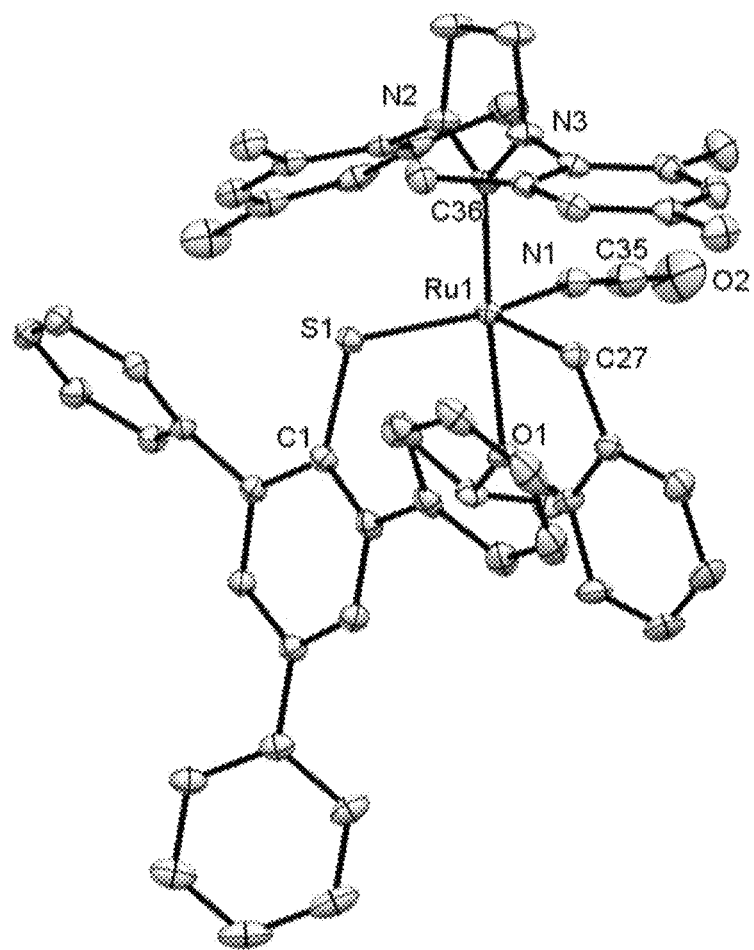
FIG. 1 shows an ORTEP-style diagram of 4a with the displacement ellipsoids drawn at the 50% probability level. Hydrogen atoms and the solvent molecule (dichloromethane) have been omitted for clarity. Selected geometrical parameters: Ru1-C27=1.834(2) Å, Ru1-C36=1.991(2) Å, Ru1-S1=2.3091(6) Ru1-O1=2.2272(17) Å, Ru1-N1=2.049 (2) Å, Ru1-S1-C1=110.03(8)°, N1-Ru1-S1=155.92(7)°, Ru1-N1-C35=169.1(2)°.

The present invention relates to a novel class of ruthenium and osmium olefin metathesis catalysts having a general formula (A) or (B) and isomers thereof:

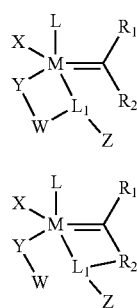

(A)

(B)

L is a N-containing heterocyclic carbene ligand;
M is ruthenium or osmium;
X is selected from the group consisting of —CN, —$N_3$, —NCO, —CNO, —NCS, and —NCSe;
Y is S, Se, or Te;
W is aryl, heteroaryl, alkyl, cycloalkyl, or heterocyclyl, wherein the aryl, alkyl, heteroaryl, cycloalkyl, or heterocyclyl is optionally substituted with 1-5 independent $CF_3$, $NO_2$, halo, CN, —C(O)—R, —C(O)OR, alkyl, optionally substituted aryl, or optionally substituted heteroaryl;

R is optionally substituted alkyl, optionally substituted alkenyl, optionally substituted alkynyl, optionally substituted heterocyclyl, optionally substituted cycloalkyl, optionally substituted aryl, or optionally substituted heteroaryl;

each $L_1$ is independently halo, N, S, or O;

each Z is independently absent or alkyl, aryl, or heteroaryl; and each $R_1$ and $R_2$ are independently hydrogen, optionally substituted alkyl, optionally substituted alkenyl, optionally substituted alkynyl, optionally substituted heterocyclyl, optionally substituted cycloalkyl, optionally substituted aryl, optionally substituted heteroaryl, or $R_1$ and $R_2$ taken together with the carbon atom to which they are attached form an optionally substituted cycloalkyl, optionally substituted heterocyclyl, optionally substituted aryl, or optionally substituted heteroaryl.

In another aspect, the invention provides a compound of Formula (C), (D), (E), or (F):

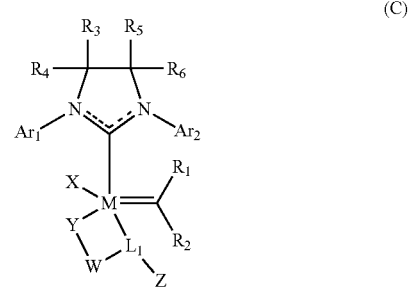

(C)

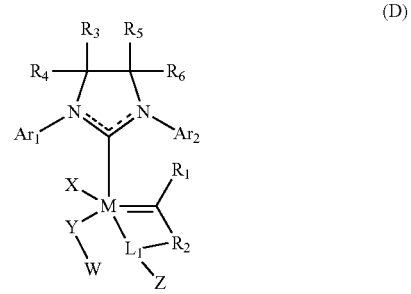

(D)

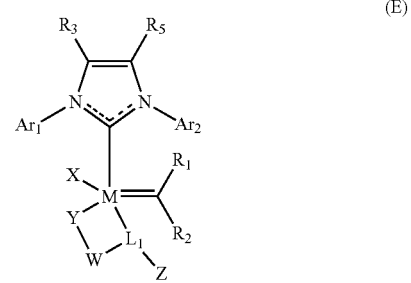

(E)

-continued (F)

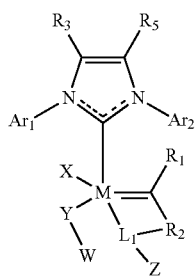

wherein each $R_3$, $R_4$, $R_5$, and $R_6$ is independently selected from the group consisting of H, $CF_3$, $NO_2$, halo, CN, —C(O)—R, —C(O)OR, optionally substituted alkyl, optionally substituted aryl, or optionally substituted heteroaryl;

$Ar_1$ and $Ar_2$ are each independently optionally substituted aryl;

M is ruthenium or osmium;

X is selected from the group consisting of —CN, —$N_3$, —NCO, —CNO, —NCS, and —NCSe;

Y is S, Se, or Te (preferably S);

W is aryl (preferably phenyl), heteroaryl, alkyl, cycloalkyl, or heterocyclyl, wherein the aryl, alkyl, heteroaryl, cycloalkyl, or heterocyclyl is optionally substituted with 1-5 independent $CF_3$, $NO_2$, halo, CN, —C(O)—R, —C(O)OR, alkyl, optionally substituted aryl, or optionally substituted heteroaryl;

R is optionally substituted alkyl, optionally substituted alkenyl, optionally substituted alkynyl, optionally substituted heterocyclyl, optionally substituted cycloalkyl, optionally substituted aryl, or optionally substituted heteroaryl;

each $L_1$ is independently halo, N, S, or O;

each Z is independently absent or alkyl, aryl, or heteroaryl; and each $R_1$ and $R_2$ are independently hydrogen, optionally substituted alkyl, optionally substituted alkenyl, optionally substituted alkynyl, optionally substituted heterocyclyl, optionally substituted cycloalkyl, optionally substituted aryl, optionally substituted heteroaryl, or $R_1$ and $R_2$ taken together with the carbon atom to which they are attached form an optionally substituted cycloalkyl, optionally substituted heterocyclyl, optionally substituted aryl, or optionally substituted heteroaryl.

In another aspect, the invention provides a compound of Formula (G), (H), (I), or (J):

(G)

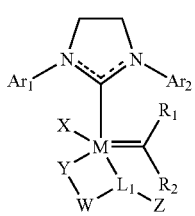

(H)

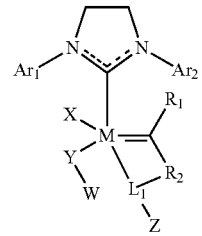

(I)

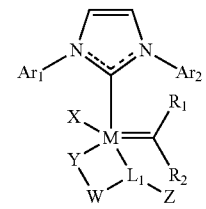

(J)

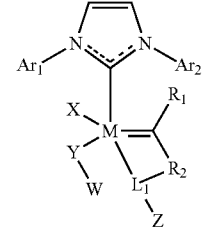

wherein $Ar_1$ and $Ar_2$ are each independently optionally substituted aryl;

M is ruthenium or osmium;

X is selected from the group consisting of —CN, —$N_3$, —NCO, —CNO, —NCS, and —NCSe;

Y is S, Se, or Te (preferably S);

W is aryl (preferably phenyl), heteroaryl, alkyl, cycloalkyl, or heterocyclyl, wherein the aryl, alkyl, heteroaryl, cycloalkyl, or heterocyclyl is optionally substituted with 1-5 independent $CF_3$, $NO_2$, halo, CN, —C(O)—R, —C(O)OR, alkyl, optionally substituted aryl, or optionally substituted heteroaryl;

R is optionally substituted alkyl, optionally substituted alkenyl, optionally substituted alkynyl, optionally substituted heterocyclyl, optionally substituted cycloalkyl, optionally substituted aryl, or optionally substituted heteroaryl;

each $L_1$ is independently halo, N, S, or O;

each Z is independently absent or alkyl, aryl, or heteroaryl; and each $R_1$ and $R_2$ are independently hydrogen, optionally substituted alkyl, optionally substituted alkenyl, optionally substituted alkynyl, optionally substituted heterocyclyl, optionally substituted cycloalkyl, optionally substituted aryl, optionally substituted heteroaryl, or $R_1$ and $R_2$ taken together with the carbon atom to which they are attached form an optionally substituted cycloalkyl, optionally substituted heterocyclyl, optionally substituted aryl, or optionally substituted heteroaryl.

In any of the embodiments presented herein, W is phenyl optionally substituted with 1-5 independent $CF_3$, $NO_2$, halo, CN, —C(O)—R, —C(O)OR, alkyl, optionally substituted aryl, or optionally substituted heteroaryl.

In any of the embodiments presented herein, W is phenyl substituted with 1-3 independent alkyl.

In any of the embodiments presented herein, W is phenyl substituted with 1-3 independent aryl (e.g., phenyl).

In any of the embodiments presented herein, Y is S and W is phenyl substituted with 1-3 independent aryl (e.g., phenyl).

In any of the embodiments presented herein, $Ar_1$ and $Ar_2$ are each independently substituted phenyl (preferably mesityl or (2,6-diisopropyl)phenyl).

In another aspect, the invention provides a compound selected from the group consisting of:

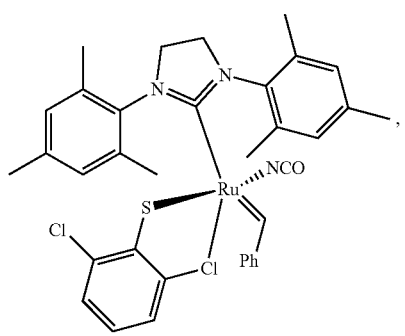

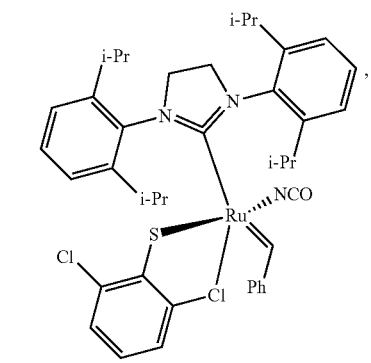

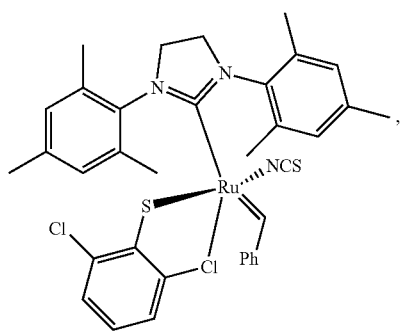

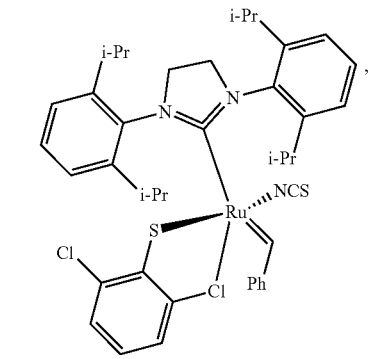

-continued

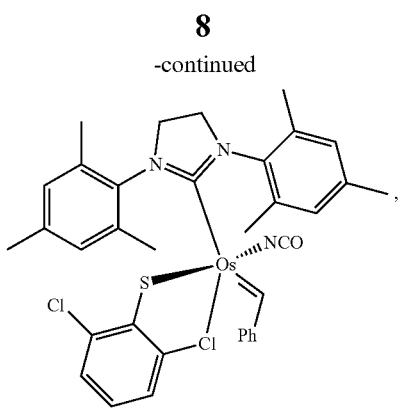

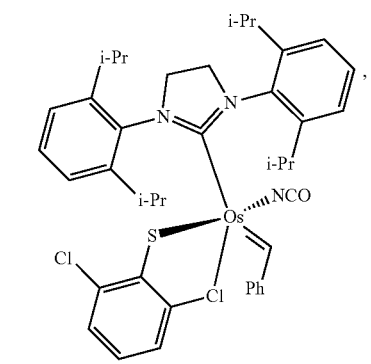

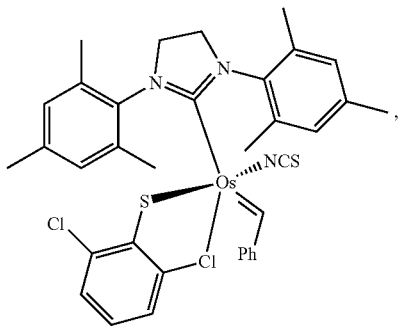

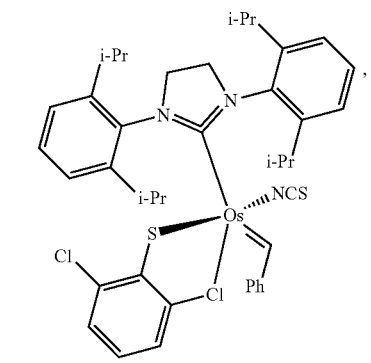

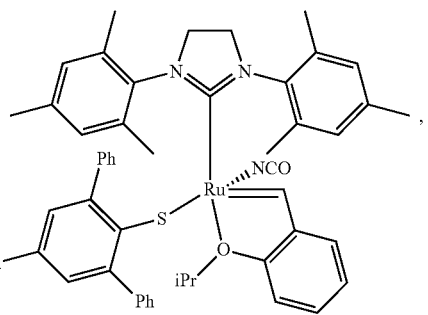

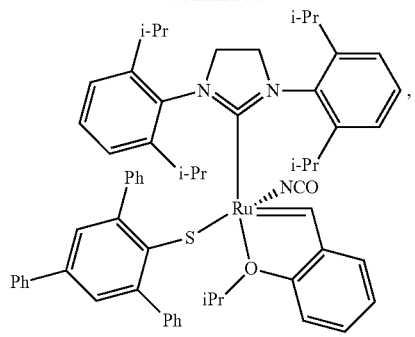
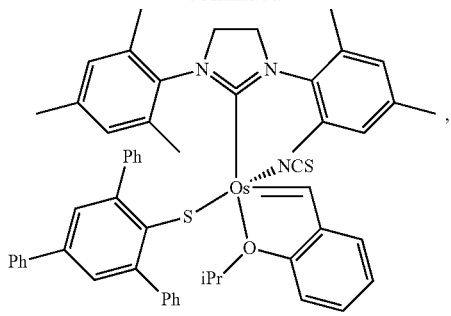
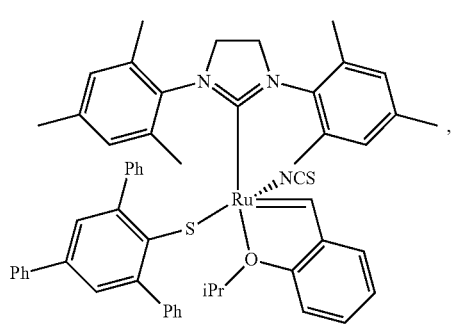
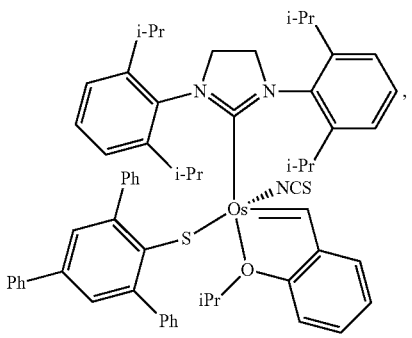
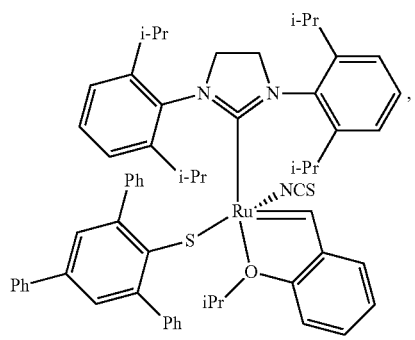
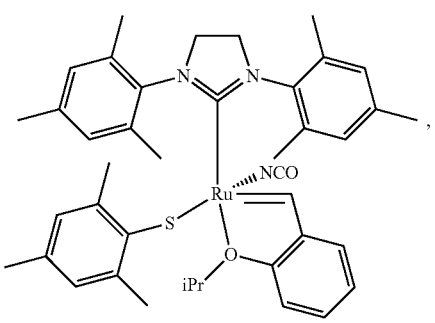
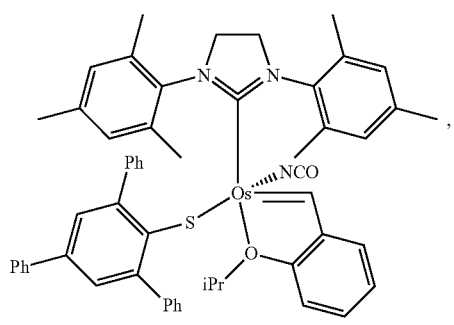
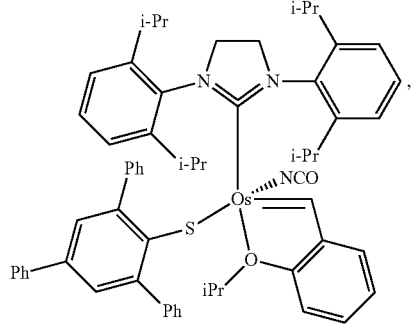
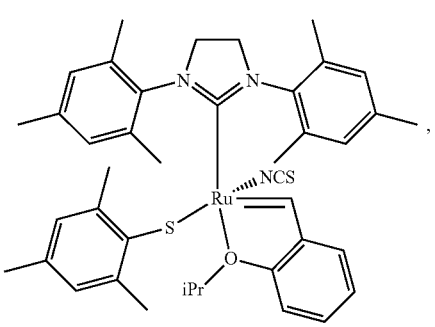

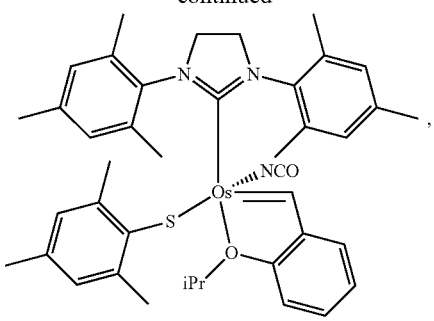

,

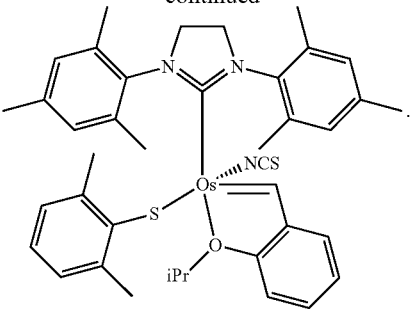

.

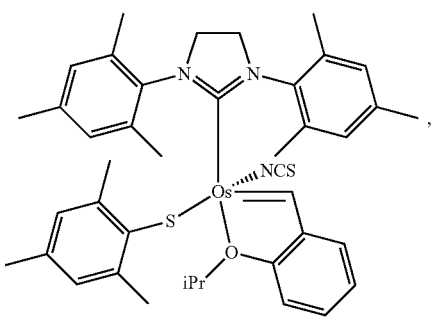

,

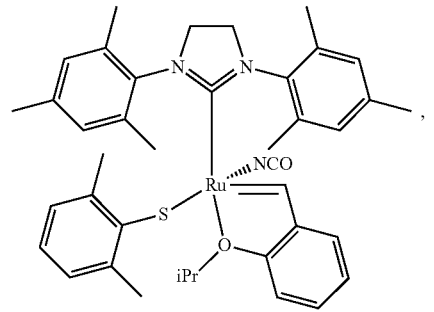

,

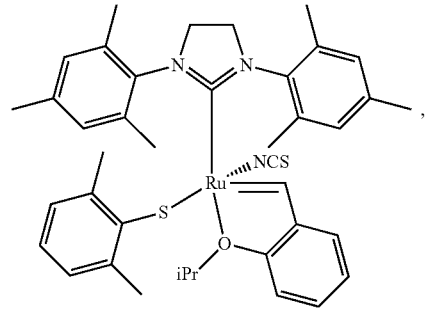

,

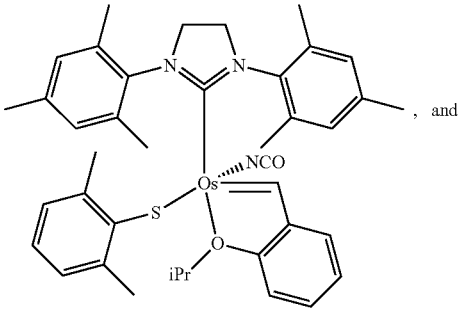

, and

In another aspect, the compound of the formulae herein is any compound delineated herein. In another aspect, the compound of the formulae herein is that wherein the compound is selected from the group 4b, 4c, 8a, 10d, 12a, 14b, or 17a.

A further aspect of the present invention is wherein any compounds of the formulae presented herein is more stable in an oxygen-containing environment (e.g., air, oxygen-enriched atmosphere, or non-degassed solvent or solvent mixture) or acidic media (e.g., a) protic solvent; b) aprotic acidic solvent; c) Brønsted acid neat, dissolved or suspended in a solvent or reaction mixture; d) Lewis acid neat, dissolved or suspended in a solvent or reaction mixture; e) solvent mixture containing one or more solvents wherein said solvent mixture comprises at least one protic or aprotic acidic solvent; or f) solvent or solvent mixture wherein said solvent or solvent mixture comprises at least one solvent that has not been degassed) than (1,3-Bis-(2,4,6-trimethylphenyl)-2-imidazolidinylidene)dichloro(o-isopropoxyphenylmethylene)ruthenium or (2,4,6-triphenylbenzenethiolate)-(Cl)-(1,3-dimesityl-4,5-dihydroimidazol-2-ylidene)-(2-isopropoxybenzylidene)-ruthenium. In a further aspect, the acidic media is phenylphosphoric acid.

A further aspect of the present invention is a catalyst for catalysing olefin metathesis reactions comprising a compound as described above. Preferably, the catalyst is capable of stereoselectively generating Z-isomeric products in olefin metathesis reactions.

In the compounds of Formula (A) or (B), L is a N-containing heterocyclic carbene ligand, which may be optionally substituted. Examples of N-containing heterocyclic carbene ligands are N,N'-bis-(mesityl) imidazol-2-ylidene (IMes), N,N'-bis-(mesityl)-4,5-dihydroimidazol-2-ylidene ($H_2$IMes), N,N'-bis-[2,6-bis(1-methylethyl)phenyl]4,5-dihydro-imidazol-2-ylidene, N,N'-bis-($C_3$-$C_{12}$ aryl or $C_1$-$C_{12}$ alkyl) imidazol-2-ylidene, and N,N'-bis-($C_3$-$C_{12}$ aryl or $C_1$-$C_{12}$ alkyl)-4,5-dihydroimidazol-2-ylidene. Optionally, the C—C backbone of the imidazol-2-ylidene or of the imidazolidine ring can have one or more hydrogen atoms substituted by aryl or preferably by alkyl groups not linked together or covalently linked to form rings.

In the compounds of Formula (A) or (B), W is an optionally substituted aryl, optionally substituted heteroaryl, optionally substituted alkyl, optionally substituted cycloalkyl, or optionally substituted heterocyclyl. In a preferred embodiment, W is optionally substituted phenyl. In other instances, W may optionally be substituted with 1-5 independent $CF_3$, $NO_2$, halo, CN, —C(O)—R, —C(O)OR, alkyl, optionally substituted aryl, or optionally substituted heteroaryl.

The groups $R^1$ and $R^2$ are each independently selected from hydrogen, optionally substituted alkyl, optionally substituted alkenyl, optionally substituted alkynyl, optionally substituted heterocyclyl, optionally substituted cycloalkyl, optionally substituted aryl, optionally substituted heteroaryl, or $R^1$ and $R^2$ taken together with the carbon atom to which they are attached form an optionally substituted cycloalkyl, optionally substituted heterocyclyl, optionally substituted aryl, or optionally substituted heteroaryl. For example, $R^1$ and $R^2$ are independently selected from the group consisting of H, $C_{1-20}$ alkyl, $C_{2-20}$ alkenyl, $C_{2-20}$ alkynyl, $C_{1-20}$ alkoxy, $C_{2-20}$ alkenyloxy, $C_{6-14}$ aryl, $C_6$-14 aryloxy, $C_{1-20}$ alkylcarboxylate, $C_{2-20}$ alkoxycarbonyl, $C_{1-20}$ alkylthio, $C_{1-20}$ alkylsufinyl or $C_{1-20}$ alkylsulfonyl, each optionally substituted with $C_{1-5}$ (halo) alkyl, halo, $C_{1-5}$ (halo) alkoxy, or phenyl optionally substituted with halo, $C_{1-5}$ (halo) alkyl or $C_{1-5}$ (halo) alkoxy.

According to an especially preferred embodiment of the present invention, 1) Y is S or Se, and 2) W is selected from the group consisting of 2,4,6-triphenyl-phenyl, 2,4,6-diphenylmethyl-phenyl, 2,4,6-tris(trifluoromethyl)-phenyl, 2,6-dimethyl-phenyl, 2,6-dichloro-phenyl or 2,3,4,5,6-pentachloro-phenyl. Further preferred embodiments of W are:

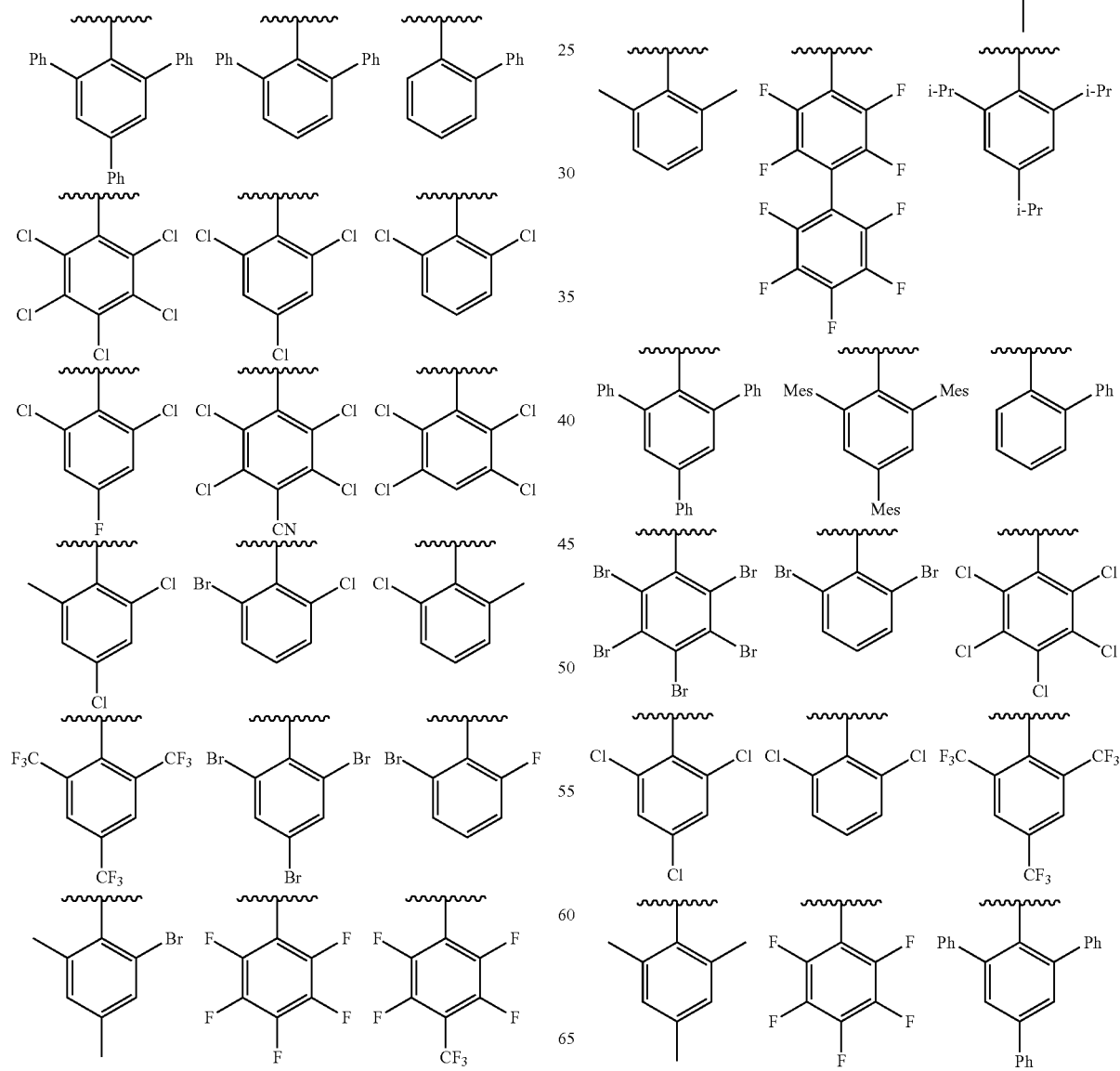

-continued

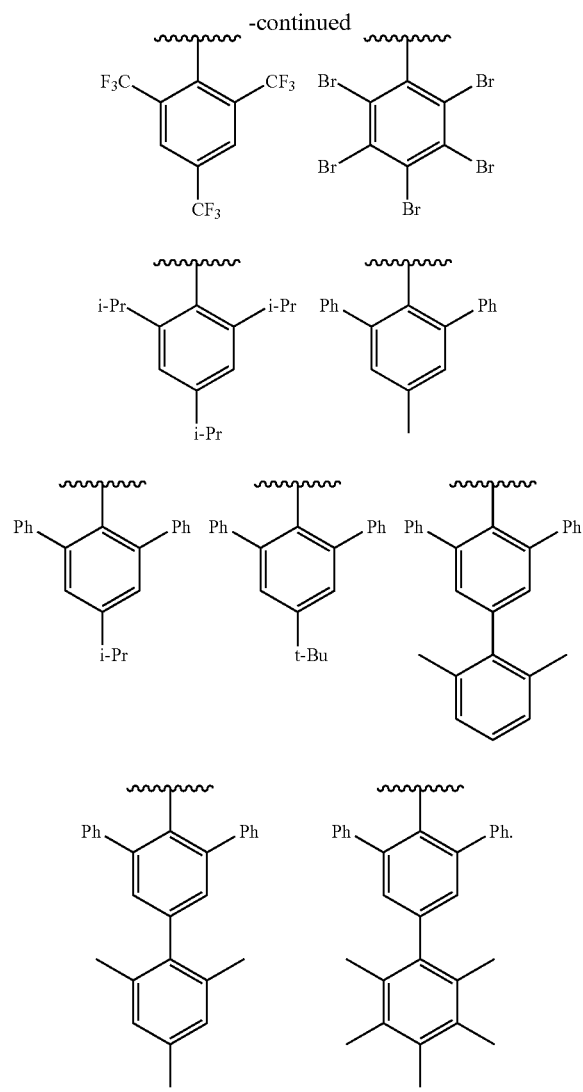

The compounds of the present invention are suitable as catalysts, e.g. for catalysing olefin metathesis reactions. The olefin metathesis reaction may comprise a reaction selected from ring-closing metathesis, ring-opening metathesis, metathesis homocoupling, cross-metathesis, ring opening metathesis polymerization, and ring opening/cross metathesis. Preferred reactions are metathesis homocoupling, cross-metathesis, and ring-closing metathesis.

In preferred aspects, the catalysts are capable of stereoselectively and/or regioselectively generating Z-isomeric products under reaction conditions containing an oxygen-containing environment (e.g., air, oxygen-enriched atmosphere, or non-degassed olefinic substrate and/or non-degassed solvent or solvent mixture) or acidic media (e.g., a) protic solvent; b) aprotic acidic solvent; c) Brønsted acid neat, dissolved or suspended in a solvent or reaction mixture; d) Lewis acid neat, dissolved or suspended in a solvent or reaction mixture; e) solvent mixture containing one or more solvents wherein said solvent mixture comprises at least one protic or aprotic acidic solvent; or f) solvent or solvent mixture wherein said solvent or solvent mixture comprises at least one solvent that has not been degassed).

In especially preferred aspects, the catalysts are capable of stereoselectively generating Z-isomeric products in ring-closing metathesis reactions. In representative catalysed olefin metathesis reactions the Z/E selectivity using the novel catalysts is at least 10%, at least 20% or at least 30% (calculated on the total yield of Z and E products) higher than that obtained using (1,3-Bis-(2,4,6-trimethylphenyl)-2-imidazolidinylidene)dichloro(o-isopropoxyphenylmethylene)ruthenium. In representative catalysed olefin metathesis reactions the Z/E selectivity using the novel catalysts is at least 10%, at least 20% or at least 30% (calculated on the total yield of Z and E products) higher than that obtained using 2,4,6-triphenylbenzenethiolate)-(Cl)-(1,3-dimesityl-4,5-dihydroimidazol-2-ylidene)-(2-isopropoxybenzylidene)-ruthenium.

In preferred aspects, the catalysts are capable of stereoselectively and/or regioselectively generating Z-isomeric products. In especially preferred aspects, the catalysts are capable of stereoselectively generating Z-isomeric products in ring-closing metathesis reactions. In representative catalysed olefin metathesis reactions the Z/E selectivity using the novel catalysts is at least 10%, at least 20% or at least 30% (calculated on the total yield of Z and E products) higher than that obtained using (1,3-Bis-(2,4,6-trimethylphenyl)-2-imidazolidinylidene)dichloro(o-isopropoxyphenylmethylene)ruthenium. In representative catalysed olefin metathesis reactions the Z/E selectivity using the novel catalysts is at least 10%, at least 20% or at least 30% (calculated on the total yield of Z and E products) higher than that obtained using 2,4,6-triphenylbenzenethiolate)-(Cl)-(1,3-dimesityl-4,5-dihydroimidazol-2-ylidene)-(2-isopropoxybenzylidene)-ruthenium.

In other aspects, the invention provides for a method of catalysing an olefin metathesis reaction comprising introducing any compound presented herein in a reaction medium comprising an olefin.

In other aspects, the method of catalysing an olefin metathesis reaction comprising introducing a compound selected from the group consisting of:

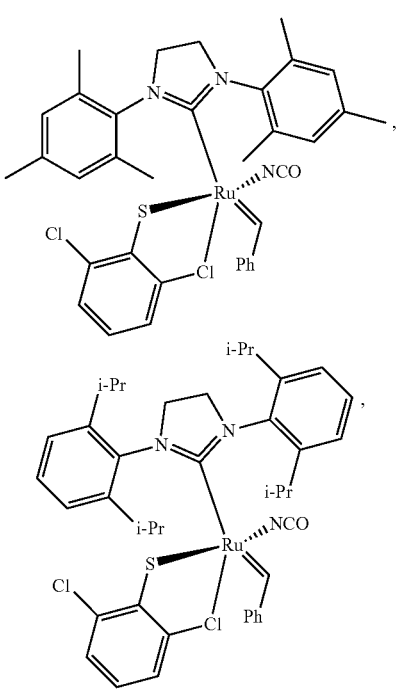

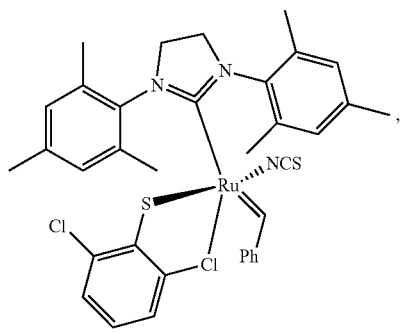
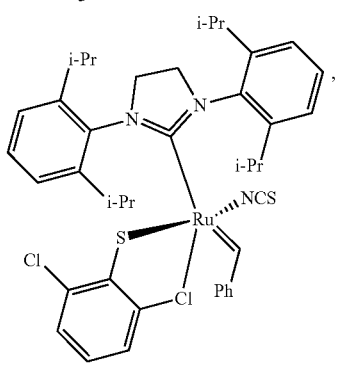
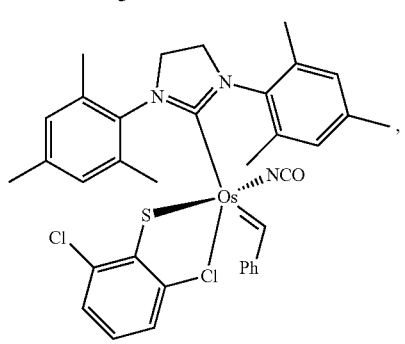
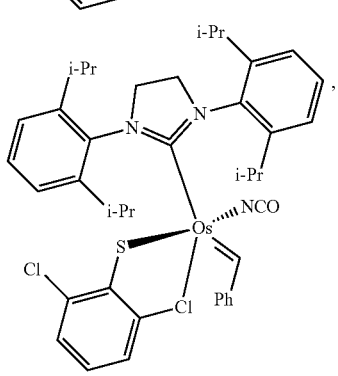
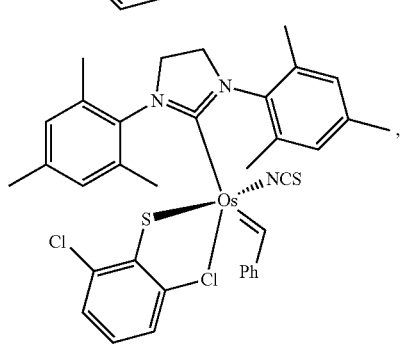
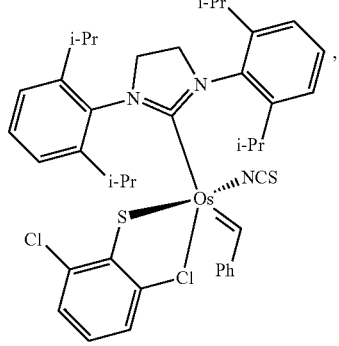
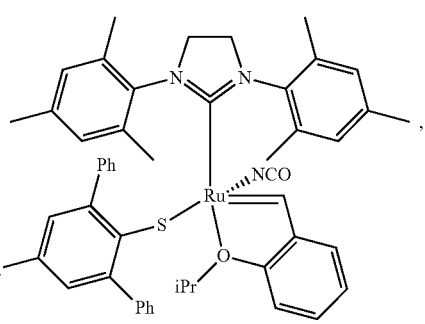
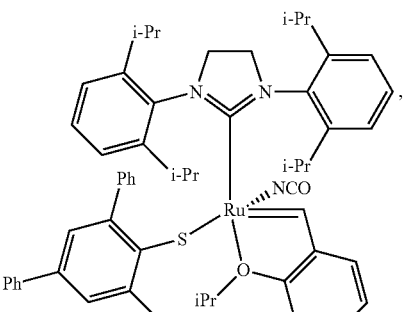
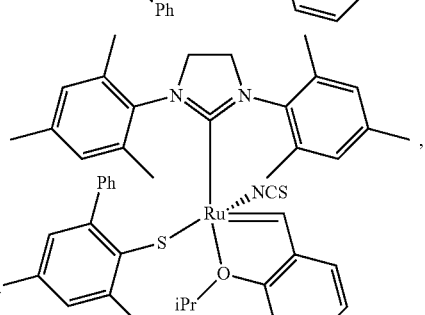
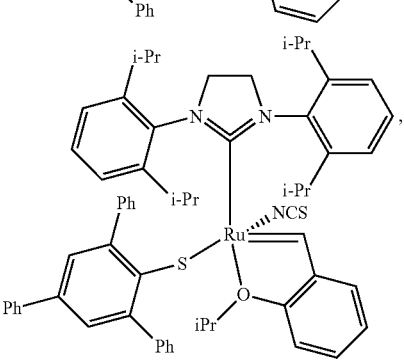

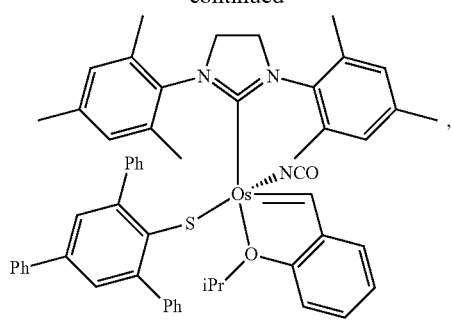
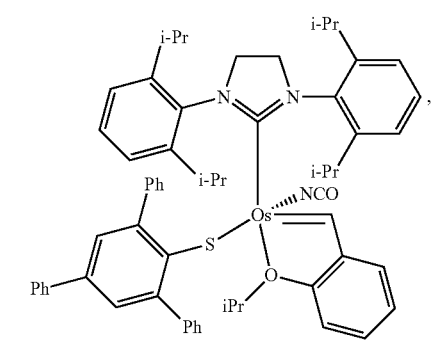
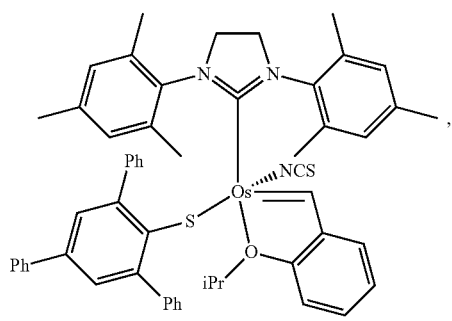
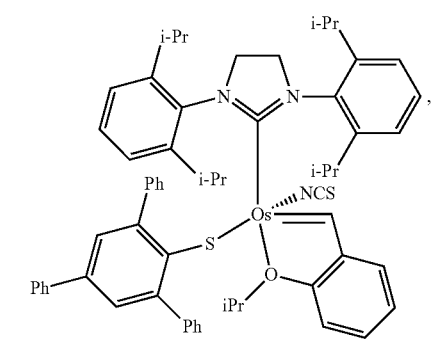
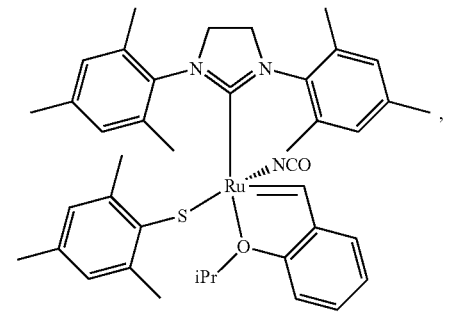
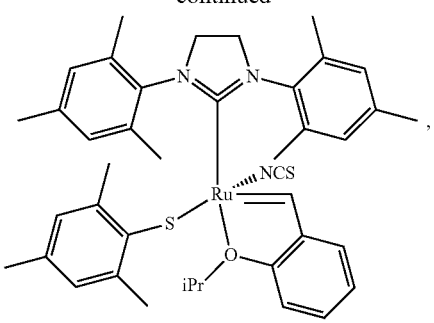
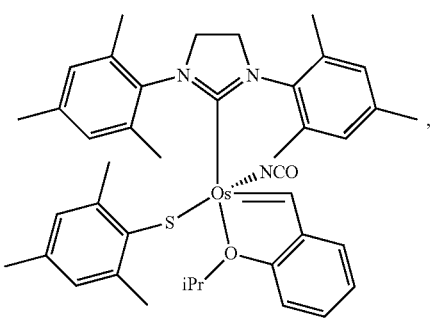
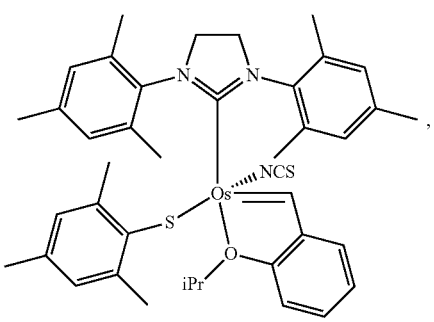
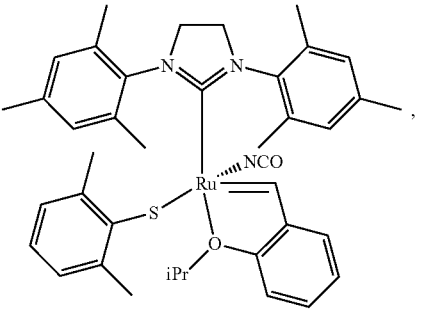
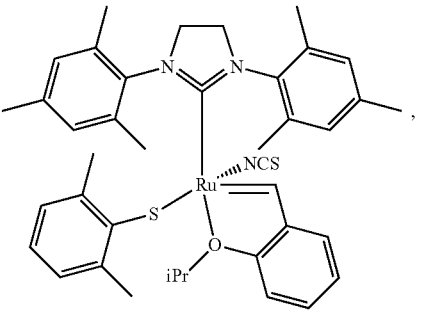

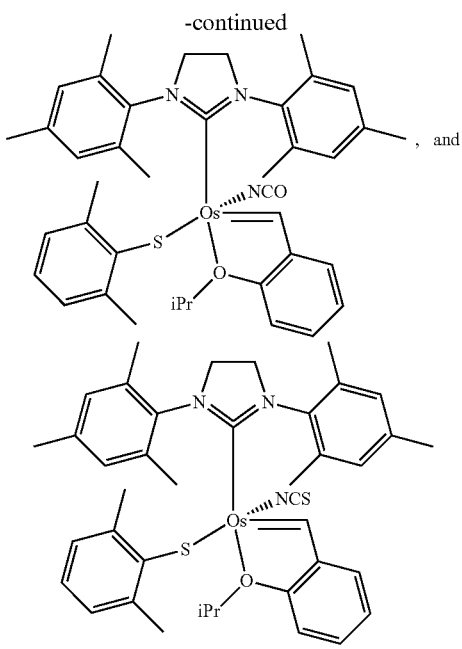

, and in a reaction medium comprising an olefin.

In other aspects, the olefin metathesis reaction comprises reactions selected from ring-closing metathesis, ring-opening metathesis, metathesis homocoupling, cross-metathesis, ring opening metathesis polymerization, or ring opening/cross metathesis.

In other aspects, the method stereoselectively and/or regioselectively generates disubstituted olefin products in a ring-closing metathesis, ring-opening metathesis, metathesis homocoupling, cross-metathesis, ring opening metathesis polymerization reaction, or ring opening/cross metathesis.

In any of the embodiments presented herein, the ring-closing metathesis, ring-opening metathesis, metathesis homocoupling, cross-metathesis, ring opening metathesis polymerization, or ring opening/cross metathesis. reaction further comprises an oxygen-containing environment (e.g., air, oxygen-enriched atmosphere, or a non-degassed olefinic substrate and/or solvent or solvent mixture) or acidic media (e.g., a) protic solvent; b) aprotic acidic solvent; c) Brønsted acid neat, dissolved or suspended in a solvent or reaction mixture; d) Lewis acid neat, dissolved or suspended in a solvent or reaction mixture; e) solvent mixture containing one or more solvents wherein said solvent mixture comprises at least one protic or aprotic acidic solvent; or f) solvent or solvent mixture wherein said solvent or solvent mixture comprises at least one solvent that has not been degassed. In another aspect, the method results in products where the Z/E selectivity is at least 10% (calculated on the total yield of Z and E products) higher than that obtained using (2,4,6-triphenylbenzenethiolate)-(Cl)-(1,3-dimesityl-4,5-dihydroimidazol-2-ylidene)-(2-isopropoxybenzylidene)-ruthenium. In another aspect, the method results in products where the Z/E selectivity is at least 10% (calculated on the total yield of Z and E products) higher than that obtained using (1,3-Bis-(2,4,6-trimethylphenyl)-2-imidazolidinylidene)dichloro(o-isopropoxyphenylmethylene)ruthenium. In a further aspect, the acidic media is phenylphosphoric acid.

The recitation of a listing of chemical groups in any definition of a variable herein includes definitions of that variable as any single group or combination of listed groups.

The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

The catalyst of the present invention may be free in the reaction medium or bound to a solid support, e.g. inorganic supports such as glass beads, or magnetic beads, or organic supports such as sepharose or polystyrene.

Compounds according to the present invention were characterised and/or provided by density functional theory calculations as well as by experimental reactions.

Definitions

In order that the invention may be more readily understood, certain terms are first defined here for convenience.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Furthermore the compounds of the invention include olefins having either geometry: "Z" refers to what is referred to as "cis" (same side) configuration whereas "E" refers to what is referred to as "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" or "heterocyclyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thienyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N''-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, $2^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention.

The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more.

The term "salts" is meant to include salts of the compounds which are prepared with acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

2. Experimental

The synthesis of the organometallic complexes and some of the catalytic tests were performed under a dry argon atmosphere, either inside a glovebox or using Schlenk techniques, unless otherwise stated. Tetrahydrofuran (THF), dichloromethane, and toluene were dried and degassed using an MBraun solvent purification system ("Grubbs' column"), while dry pentane was purchased from Sigma-Aldrich and used as received. Tetrahydrofuran used in the catalytic test conducted in air was purchased from Sigma Aldrich and stored in air atmosphere. The ruthenium complexes 15, 9, and 11 were purchased from Sigma Aldrich while complex 13 was purchased from Strem Chemicals. The ruthenium complexes 4 (30) and 16 (31) were prepared according to literature procedures. The olefinic substrates were purchased from Sigma-Aldrich and used as received. For selected catalytic tests 1-octene, allylbenzene, 4-phenyl-1-butene, allylacetate, allyl trimethylsilane, and methyl undecenoate were degassed before use. 2,4,6-Triphenylbenzenethiophenol, and sodium benzenethiolate (2d) were purchased from Sigma aldrich, while 5'-(2''',6'''-dimethylphenyl)-[1,1':3',1''-Terphenyl)-2'-thiol and 5'-(2''',4'''-ditrifluoromethylphenyl)-[1,1':3',1''-Terphenyl)-2'-thiol were purchased from Santai Labs and used as received. All the other chemicals were purchased from Sigma-Aldrich, TCI Europe and used as received.

Potassium 2,4,6-triphenylbenzenethiolate (2a) was prepared according to literature procedure. (32) Potassium thiolate 2b and 2c were prepared using the following procedure: In a glovebox, KH (1.43 mmol) was added in small portions to a stirred solution of the corresponding thiol (i.e. 5'-(2''',6'''-dimethylphenyl)-[1,1':3',1''-Terphenyl)-2'-thiol (2b) and 5'-(2''',4'''-ditrifluoromethylphenyl)-[1,1':3',1''-Terphenyl)-2'-thiol (2c)) (1.36 mmol) in THF (5 mL). The mixture was stirred at room temperature for 24 hours.

Compound 2b which has a low solubility in THF, was isolated by cannula filtration outside the glovebox using a Schlenk line, then washed twice with THF (5 mL) at room temperature, and finally dried inside the glove box to give a white powder (481 mg, 82% of yield). Compound 2c, which on the contrary possesses a good solubility in THF, was isolated as a yellow pale solid, by removal of the solvent under vacuum and used without further purification. The quality of the product was evaluated by 1H-NMR spectroscopy, which showed the disappearance of the thiol proton peak at 3.49 (2b) and 3.54 (2c) ppm (CDCl3) respectively.

Hoveyda-Grubbs second-generation catalyst (3), silver cyanate, silver thiocyanate, 2,4,6-triphenylbenzenethiol (1), 1,3,5-tri-tert-butylbenzene, ethyl acetate, and dichloromethane-$d_2$ were purchased from Sigma-Aldrich and used as received. Chloroform-d was purchased from Sigma-Aldrich, dried under $CaH_2$ and distilled prior use. Phenylphosphoric acid was purchased from TCI and used as received. Bis(isocyanato)-(1,3-dimesityl-4,5-dihydroimidazol-2-ylidene)-2-isopropoxybenzylidene)-ruthenium (4), and Bis(isothiocyanato)-(1,3-dimesityl-4,5-dihydroimidazol-2-ylidene)-2-isopropoxybenzylidene)-ruthenium (5), and (2,4,6-triphenylbenzenethiolate)-(Cl)-(1,3-dimesityl-4,5-dihydroimidazol-2-ylidene)-2-isopropoxybenzylidene)-ruthenium (3a) were prepared according literature procedures (28, 30), see Chart 1.

Chart 1. Known olefin metathesis catalysts

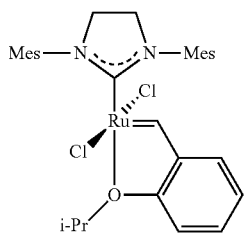

3

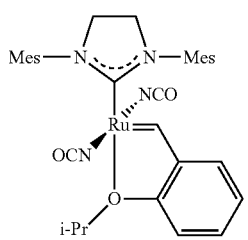

4

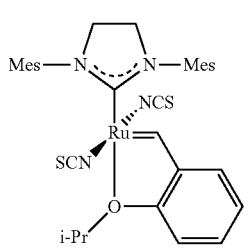

5

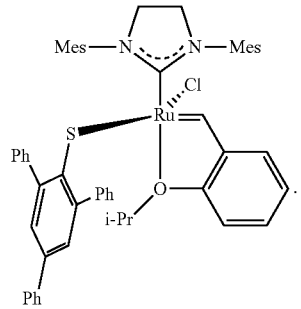

3a

The olefinic substrates allylacetate, 1-octene, and allylbenzene were purchased from Sigma-Aldrich and degassed before use. Allyltrimethylsilane and methyl undecenoate were purchased from Sigma-Aldrich and used as received.

Potassium 2,4,6-triphenylbenzenethiolate (2) used as starting material in examples 1 and 2 was prepared using a procedure slightly modified from that previously reported from our group (27, 28):

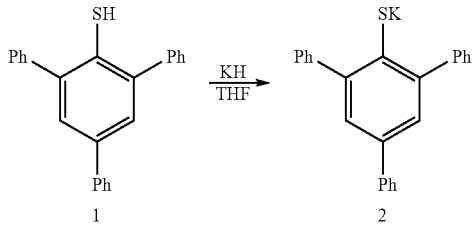

In a glovebox, KH (3.10 mmol) was added in small portions to a stirred solution of 2,4,6-triphenylbenzenethiol (2.95 mmol) in THF (10 mL). The mixture was stirred at room temperature for 24 hours. The product, a white solid, was isolated by cannula filtration outside the glovebox using a Schlenk line, then washed twice with THF (7 mL) at room temperature, and finally dried under vacuum.

NMR spectra were recorded on a Bruker Biospin DPX400, AV500, and AV600 spectrometers. The chemical shifts are reported relative to the residual solvent peaks.

DART-MS spectra were recorded by means of a DART-100 ion source from IonSense Inc. (Saugus, Mass., USA) interfaced to an AccuTOF™ atmospheric ionization mass spectrometer from JEOL USA, Inc. (Peabody, Mass., USA). X-ray diffraction measurements were performed on a Bruker Apex Ultra TXS, rotating anode, CCD instrument doing 0.3-0.5 degree ω scans over 182° in four orthogonal φ-settings. The samples were cooled using a $N_2$ blower, series 700 from Oxford Cryosystem. Apart from geometrical corrections, numerical absorption correction by face indexing with Gaussian quadrature integration, and semi-empirical incident beam correction were applied.

The AccuTOF™ mass spectrometer was operated with an orthogonal electrospray ionization source (ESI), an orthogonal accelerated time of flight (TOF) single stage reflectron mass analyzer and a dual micro channel plate (MCP) detector.

Example 1: Preparation of Ruthenium Complex 4a

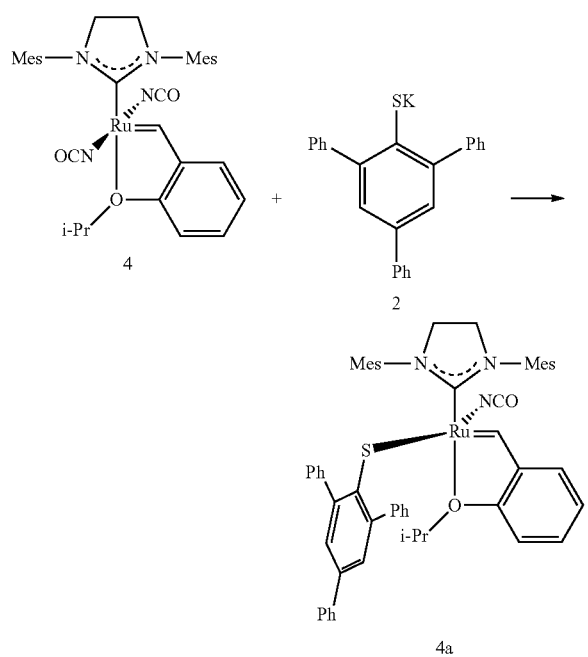

In a glovebox, bis(isocyanato)-(1,3-dimesityl-4,5-dihydroimidazol-2-ylidene)-2-isopropoxybenzylidene)-ruthenium 4 (440 mg, 0.67 mmol), and potassium 2,4,6-triphenylthiophenolate 2 (265 mg, 0.70 mmol) were transferred to a 50 mL Schlenk flask, followed by addition of 10 mL of THF, and the mixture was stirred at room temperature for 24 hours. $^1$H NMR analysis of the reaction mixture revealed the presence of about 0.2% of the starting material 4 (estimated by integration of the singlet at 4.16 ppm (CDCl$_3$) corresponding to the four hydrogen atoms of the C—C backbone of the imidazoline moiety of the N,N'-bis-(mesityl)-4,5-dihydroimidazol-2-ylidene (H$_2$IMes). The mixture was filtrated through Celite using THF as solvent, followed by removal of the solvent in vacuo. To the residual potassium salt 2 (13 mg, 0.034 mmol) and 5 ml of THF were added, and the mixture was stirred at room temperature for another 24 hours. $^1$H NMR analysis of the reaction mixture showed complete conversion of the starting material 4 to the target product 4a. The mixture was first filtrated through Celite using THF as solvent, followed by removal of the solvent in vacuo. The residual was redissolved in 3 mL CH$_2$Cl$_2$, and then pentane (40 ml) was slowly added, in such a way to obtain two separate layers, which were allowed to diffuse slowly (one week) toward each other at −32° C. The grown crystals of 4a.CH$_2$Cl$_2$ (622 mg, yield 91%) were then collected, washed three times with pentane, and dried in argon atmosphere. A suitable crystal was selected for X-ray diffraction analysis. The molecule of solvent (CH$_2$Cl$_2$) present in the crystal lattice is slowly lost with time. $^1$H NMR (600.17 MHz, CD$_2$Cl$_2$): δ=14.32 (s, 1H), 7.73-7.47 (m, 5H), 7.44-7.39 (m, 2H), 7.37-7.29 (m, 3H), 7.26-7.21 (m, 1H), 7.15 (s, br, 1H), 6.99 (t, br, J=6.9 Hz, 1H), 6.95 (s, br, 2H), 6.89-6.64 (m, 8H), 6.56-6.48 (m, 2H), 4.23 (sept, J=6.1 Hz, 1H), 3.92 (s, br, 4H), 2.36 (s, 6H), 2.33 (s, 6H), 2.13 (s, 6H), 0.84 (d, J=6.1 Hz, 3H), 0.53 (d, J=6.1 Hz, 3H). $^{13}$C{$^1$H} NMR (150.91 MHz, CD$_2$Cl$_2$): δ=276.88, 276.83, 209.50, 153.80, 149.33, 147.33, 145.55, 145.27, 142.34, 141.54, 140.99, 138.47, 138.37, 138.28, 137.04, 136.13, 131.33, 131.20, 129.55, 129.13, 129.07, 128.95, 128.50, 128.34, 128.17, 127.84, 127.69, 127.24, 126.93, 125.69, 122.82, 121.95, 113.04, 76.23, 51.85, 21.18, 20.90, 20.59, 19.03, 18.68. HRMS (ESI$^+$), m/z: 955.29851 [M+Na]$^+$; calculated for C$_{56}$H$_{55}$N$_3$NaO$_2$$^{99}$RuS: 955.29721. Elemental analysis, calculated for C$_{56}$H$_{55}$N$_3$O$_2$SRu.0.5CH$_2$Cl$_2$; C, 69.41; H, 5.77; N, 4.30. found. C, 69.46; H, 5.75; N, 4.20.

FIG. 1 shows an ORTEP-style diagram of 4a with the displacement ellipsoids drawn at the 50% probability level. Hydrogen atoms and the solvent molecule (dichloromethane) have been omitted for clarity. Selected geometrical parameters: Ru1-C27=1.834(2) Å, Ru1-C36=1.991(2) Å, Ru1-S1=2.3091(6) Ru1-O1=2.2272(17) Å, Ru1-N1=2.049(2) Å, Ru1-S1-C1=110.03(8)°, N1-Ru1-S1=155.92(7)°, Ru1-N1-C35=169.1(2)°.

TABLE 2

Crystal data and structure refinement for complex 4a.

| | |
|---|---|
| Empirical formula | C$_{57}$ H$_{57}$ Cl$_2$ N$_3$ O$_2$ Ru S |
| Formula weight | 1020.08 |
| Temperature | 103(2) K |
| Wavelength | 0.71073 Å |
| Crystal system | Monoclinic |
| Space group | P 21/n |
| Unit cell dimensions | a = 12.4372(12) Å  α = 90°. |
| | b = 11.7065(11) Å  β = 95.4840(10)°. |
| | c = 34.327(3) Å  γ = 90°. |
| Volume | 4975.0(8) Å$^3$ |
| Z | 4 |
| Density (calculated) | 1.362 Mg/m$^3$ |
| Absorption coefficient | 0.510 mm$^{-1}$ |
| F(000) | 2120 |
| Crystal colour/habit | Dark purple/Flat pinacoid prism |
| Crystal size | 0.449 × 0.292 × 0.228 mm$^3$ |
| Theta range for data collection | 1.802 to 30.597°. |
| Index ranges | −17 <= h <= 17, −16 <= k <= 16, −49 <= l <= 49 |
| Reflections collected | 81198 |
| Independent reflections | 15194 [R(int) = 0.0582] |
| Completeness to theta = 25.242° | 99.8% |
| Absorption correction | Numerical by face indexing |
| Refinement method | Full-matrix least-squares on F$^2$ |
| Data/restraints/parameters | 15194/0/606 |
| Goodness-of-fit on F$^2$ | 1.138 |
| Final R indices [I > 2sigma(I)] | R1 = 0.0537, wR2 = 0.1330 |
| R indices (all data) | R1 = 0.0605, wR2 = 0.1369 |
| Extinction coefficient | n/a |
| Largest diff. peak and hole | 1.746 and −1.650 e.Å$^{-3}$ |

Example 2: Preparation of Ruthenium Complex 5a

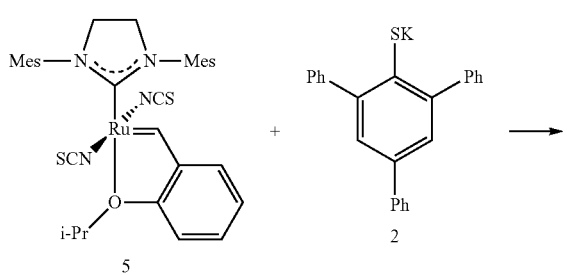

-continued

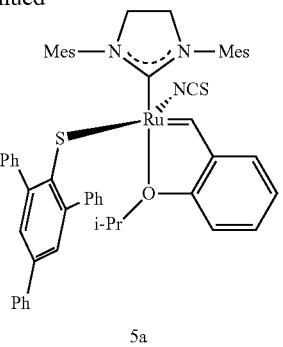

5a

In a glovebox, bis(isothiocyanato)-(1,3-dimesityl-4,5-dihydroimidazol-2-ylidene)-2-isopropoxybenzylidene)-ruthenium (5) (77 mg, 0.11 mmol) and potassium 2,4,6-triphenylthiophenolate 2 (45 mg, 0.12 mmol) were transferred to a 50 mL Schlenk flask, followed by addition of 15 mL of THF. The mixture was stirred at room temperature for 24 hours. $^1$H NMR analysis of the reaction mixture revealed the presence of about 0.9% of the starting material 5, estimated by integration of the singlet at 4.21 ppm (CDCl$_3$) corresponding to the four hydrogens of C—C backbone of the imidazoline moiety of the H$_2$IMes ligand. The mixture was filtrated through Celite using THF as solvent, followed by removal of the solvent in vacuo. To the residual potassium salt 2 (3 mg, 0.008 mmol) and 5 ml of THF were added, and the mixture was stirred at room temperature for another 24 hours. $^1$H NMR analysis of the reaction mixture showed complete conversion of the starting material 5 to the target product 5a. The mixture was filtrated through Celite, using THF as solvent, followed by removal of the solvent in vacuo. The residual was redissolved in 1 mL CH$_2$Cl$_2$, and then pentane (10 ml) was slowly added, in such a way to obtain two separate layers, which were allowed to diffuse slowly (one week) toward each other at −32° C. The grown crystals of 5a.CH$_2$Cl$_2$ (110 mg, yield 92%) were then collected, washed three times with pentane, and dried in argon atmosphere. A suitable crystal was selected for X-ray diffraction analysis. $^1$H NMR (600.17 MHz, CD$_2$Cl$_2$): δ=14.46 (s, 1H), 7.67-7.48 (m, 5H), 7.45-7.39 (m, 3H), 7.34-7.29 (m, 2H), 7.27-7.22 (m, 1H), 7.16 (s, br, 1H), 7.05-6.93 (m, 3H), 6.88 (t, J=7.4 Hz, 1H), 6.86-6.65 (m, 7H), 6.59-6.53 (m, 2H), 4.29 (sept, J=6.1 Hz, 1H), 3.94 (s, br, 4H), 2.37 (s, 6H), 2.34 (s, 6H), 2.11 (s, 6H), 0.82 (d, J=6.1 Hz, 3H), 0.53 (d, J=6.1 Hz, 3H). $^{13}$C{1H} NMR (150.91 MHz, CD2Cl2): δ=282.18, 282.15, 207.81, 154.31, 149.30, 147.22, 145.40, 145.17, 142.84, 141.38, 141.28, 140.86, 138.62, 138.40, 138.20, 137.31, 131.16, 129.73, 129.25, 129.21, 129.15, 128.97, 128.45, 128.41, 128.01, 127.78, 127.31, 127.03, 126.95, 125.75, 123.21, 122.04, 113.18, 76.92, 51.88, 21.18, 20.59, 20.51, 18.94, 18.69. HRMS (ESI$^+$), m/z: 948.28672 [M*]$^+$; calculated for C$_{56}$H$_{55}$N$_3$O$_1$$^{99}$RuS$_2$: 948.28459. Elemental analysis, calculated for C$_{56}$H$_{55}$N$_3$OS$_2$Ru—CH$_2$Cl$_2$: C, 66.07; H, 5.54; N, 4.06. found. C, 65.78; H, 5.28; N, 3.99.

Figure 2:
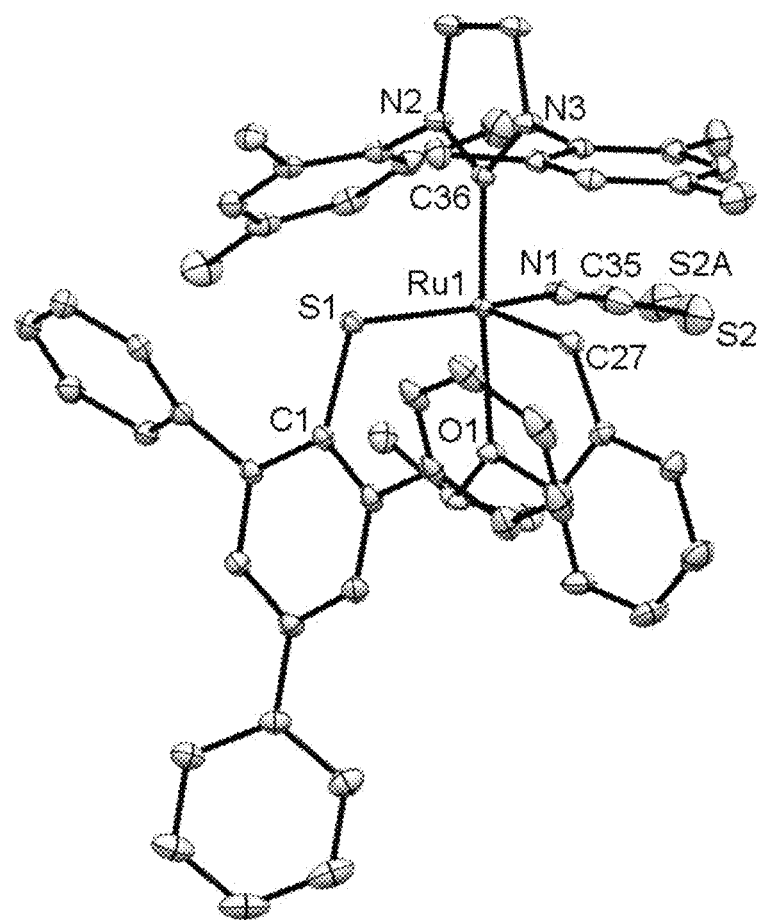
FIG. 2 shows an ORTEP-style diagram of 5a with the displacement ellipsoids drawn at the 50% probability level. The sulphur atom on NCS ligand is disordered over two position (S2 and S2A, with a 0.66:0.44 distribution respectively). There is also a disorder of the one $CH_2Cl_2$ solvent molecule over two positions which is fully correlated with the disorder of the sulphur atom. Hydrogen atoms and the solvent molecule (dichloromethane) have been omitted for clarity. Selected geometrical parameters: Ru1-C27=1.8399 (16) Å, Ru1-C36=1.9950(15) Å, Ru1-S1=2.3050(4) Ru1-O1=2.2383(11) Å, Ru1-N1=2.0435(14) Å, Ru1-S1-C1=109.78(5) °, N1-Ru1-S1=157.87(5)°, Ru1-N1-C35=166.87(16)°.

FIG. 2 shows an ORTEP-style diagram of 5a with the displacement ellipsoids drawn at the 50% probability level. The sulphur atom on NCS ligand is disordered over two position (S2 and S2A, with a 0.66:0.44 distribution respectively). There is also a disorder of the one CH$_2$Cl$_2$ solvent molecule over two positions which is fully correlated with the disorder of the sulphur atom. Hydrogen atoms and the solvent molecule (dichloromethane) have been omitted for clarity. Selected geometrical parameters: Ru1-C27=1.8399 (16) Å, Ru1-C36=1.9950(15) Å, Ru1-S1=2.3050(4) Ru1-O1=2.2383(11) Å, Ru1-N1=2.0435(14) Å, Ru1-S1-C1=109.78(5) °, N1-Ru1-S1=157.87(5)°, Ru1-N1-C35=166.87(16)°.

TABLE 3

Crystal data and structure refinement for complex 5a.

| | |
|---|---|
| Empirical formula | C$_{57}$ H$_{57}$ Cl$_2$ N$_3$ O Ru S$_2$ |
| Formula weight | 1036.14 |
| Temperature | 103(2) K |
| Wavelength | 0.71073 Å |
| Crystal system | Monoclinic |
| Space group | P 21/n |
| Unit cell dimensions | a = 12.3137(7) Å  α = 90°. |
| | b = 12.0808(6) Å  β = 94.7150(10)°. |
| | c = 33.9525(18) Å  γ = 90°. |
| Volume | 5033.7(5) Å$^3$ |
| Z | 4 |
| Density (calculated) | 1.367 Mg/m$^3$ |
| Absorption coefficient | 0.544 mm$^{-1}$ |
| F(000) | 2152 |
| Crystal colour/habit | Red/Pseudo hexagonal prism |
| Crystal size | 0.275 × 0.200 × 0.150 mm$^3$ |
| Theta range for data collection | 1.718 to 30.526°. |
| Index ranges | −17 <= h <= 17, −17 <= k <= 17, −48 <=l<= 48 |
| Reflections collected | 83841 |
| Independent reflections | 15390 [R(int) = 0.0474] |
| Completeness to theta = 25.242° | 100.0% |
| Absorption correction | Numerical by face indexing |
| Refinement method | Full-matrix least-squares on F$^2$ |
| Data/restraints/parameters | 15390/7/645 |
| Goodness-of-fit on F2 | 1.030 |
| Final R indices [I > 2sigma(I)] | R1 = 0.0379, wR2 = 0.0979 |
| R indices (all data) | R1 = 0.0436, wR2 = 0.1023 |
| Extinction coefficient | n/a |
| Largest diff. peak and hole | 1.718 and −0.950 e.Å$^{-3}$ |

Example 3: Decomposition of 3a, 4a, and 5a in Presence of Air

In a glove box, a NMR tube was charged with 0.002 mmol of complex and 0.7 mL of CD$_2$Cl$_2$ containing 1,3,5-Tri-tert-butylbenzene as an internal standard (0.001 M). The tube was closed with a plastic cap and wrapped with parafilm. A $^1$H NMR spectrum of the solution was immediately recorded. The plastic cap was then removed in the fume hood, and the solution was exposed to air for 10 minutes. The tube was again closed with the same plastic cap, wrapped with a new layer of parafilm, stored at room temperature (~20° C.), and shaken for some seconds from time to time. The decomposition of the catalyst was monitored by $^1$H-NMR, by comparing the integral of the alkylidene proton with that of the tert-butyl groups (δ=1.32 ppm (s, 27H) of the internal standard.

TABLE 4

Decomposition of complexes 3a, 4a, and 5a in presence of air

| Entry | Complex | Time, h | Decomposition, % | Formation of other Ru-alkylidene species (%) |
|---|---|---|---|---|
| 1 | 3a | 20 | 100 | 3 (6) |
| 2 | 4a | 20 | 13 | 4 (1) |
| | | one week | 49 | 4 (2)$^a$ |
| | | two weeks | 79 | 4 (2.5)$^a$ |

TABLE 4-continued

Decomposition of complexes 3a, 4a, and 5a in presence of air

| Entry | Complex | Time, h | Decomposition, % | Formation of other Ru-alkylidene species (%) |
|---|---|---|---|---|
| 3 | 5a | 20 | 4 | — |
|  |  | one week | 62 | 5 (3)[b] |
|  |  | two weeks | >99 | 5 (3)[c] |

[a]Other three peaks in the alkylidene region respectively at 14.38 ppm, 13.63 ppm, and 13.53 ppm were also detected. The overall amount of these unidentified species is about 0.8%.
[b]Other peaks in the alkylidene region respectively at 16.50 ppm, 16.45 ppm, 16.43, and 14.38 ppm) were also detected. The overall amount of these unidentified species is about 1.2%.
[c]Other peaks in the alkylidene region respectively at 16.45 ppm and 16.43 ppm were also detected. The overall amount of these unidentified species is about 0.8%.

Example 4: Decomposition of 3a, 4a, and 5a in Presence of Acids

In a glove box, a Young NMR tube was charged with 0.002 mmol of complex and 0.7 mL of $CD_2Cl_2$ containing 1,3,5-Tri-tert-butylbenzene as an internal standard (0.001 M). The tube was closed and a $^1$H-NMR spectrum of the solution was recorded.

Then, in the glove box, 0.002 mmol of phenylphosphoric acid was added to the solution. The tube was closed, shaken vigorously for some seconds from time to time and stored at room temperature (~20° C.). The decomposition of the catalyst was monitored by $^1$H NMR, by comparing the integral of the alkylidene proton with that of the tert-butyl groups (δ=1.32 ppm (s, 27H) of the internal standard.

TABLE 5

Decomposition of complexes 3a, 4a, and 5a in presence of acid

| Entry | Complex | Time, h | Decomposition, % | Formation of other Ru-alkylidene species (%) |
|---|---|---|---|---|
| 1 | 3a | 20 | 34 | 3 (16) |
|  |  | two weeks | 46 | 3 (21) |
| 2 | 4a | 20 | 2 | 4 (0.5) |
|  |  | two weeks | 7 | 4 (1)[a] |
| 3 | 5a | 20 | 4 | 5 (2) |
|  |  | two weeks | 39 | 5 (17)[b] |

[a]Other three peaks in the alkylidene region respectively at 14.75 ppm, 14.39 ppm, and 14.36 ppm were also detected. The overall amount of these unidentified species is about 0.7%.
[b]Another peak in the alkylidene region respectively at 16.45 ppm (1.8%) was also detected.

Example 5: Homocoupling of Terminal Olefins in THF (4M in Substrate)

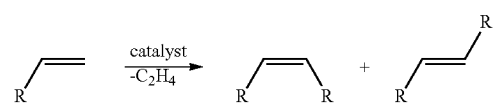

In a glove box, a 50 mL Schlenk flask equipped with a Young's tap was charged with the catalyst (5×10$^{-3}$ mmol). Next, to remove the solvent (dichloromethane) present in the crystal lattice, the following procedure was performed twice: ~0.7 mL of THF was added to the Schlenk flask to dissolve the solid, followed by removal of the solvent under reduced pressure. Then, in a glove box, the substrate (2.0 mmol) and the solvent (THF) were added to the flask to obtain 0.5 mL of a 4 M solution, and the reaction mixture was stirred and heated in an oil bath at 40° C.

TABLE 6

Metathesis homocoupling of terminal olefins in THF[a]

| entry | cata-lyst | sub-strate | DMAN[b] loading mol % | time, h | temp., ° C. | % conv.[c] | Yield[c] (isolated)[d] | % Z[c] |
|---|---|---|---|---|---|---|---|---|
| 1 | 3a | allyl-TMS | 0.12 | 18 | 60 | 22 | 12(11) | 95 |
| 2 | 4a | allyl-TMS | 0.12 | 16 | 60 | 14 | 9(6) | 96 |
| 3 | 3a | allyl-acetate | 0.12 | 4 | 40 | 16 | 16 | 82 |
| 4 | 4a | allyl-acetate | 0.12 | 1 | 40 | 2 | 2 | 68 |
| 5 | 3a | allyl-benzene | 0 | 0.5 | 40 | 38 | 12 | 80 |
|  |  |  |  | 2 |  | >99 | 14 | 39 |
| 6 | 4a | allyl-benzene | 0 | 0.5 | 40 | 20 | 6 | 88 |
|  |  |  |  | 2 |  | >99 | 10 | 56 |
| 7 | 5a | allyl-benzene | 0 | 1.5 | 40 | 17 | 5 | 77 |

[a]Catalyst loading (0.25 mol %), substrate concentration (4M).
[b]1,8-bis(dimethylamino)naphthalene (DMAN).
[c]Determined by $^1$H NMR (CDCl$_3$).
[d]Isolated yield.

Example 6: Homocoupling of Terminal Olefins (Neat Substrate)

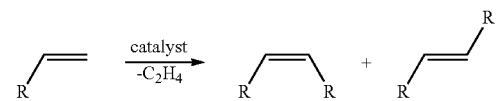

In a glove box, a 50 mL Schlenk flask equipped with a Young's tap was charged with the catalyst (6.4×10$^{-4}$ mmol). Next, to remove the solvent (dichloromethane) present in the crystal lattice, the following procedure was performed twice: ~0.7 mL of THF was added to Schlenk flask to dissolve the solid, followed by removal of the solvent under reduced pressure. Finally, in a glove box, the substrate (6.4 mmol) was added to the flask and the reaction mixture was stirred and heated in an oil bath at 60° C.

TABLE 7

Metathesis homocoupling of terminal olefins (neat substrate)

| entry | cata-lyst | sub-strate | cat. loading mol % | time, h | temp., ° C. | % conv.[b] | yield[b] (isolat-ed)[c] | % Z[b] |
|---|---|---|---|---|---|---|---|---|
| 1[b] | 3a | 1-octene | 0.01 | 4 | 60 | 24 | 20(15) | 86 |
| 2 | 4a | 1-octene | 0.01 | 4 | 60 | 20 | 13(10) | 88 |

[a]Phenylphosphoric acid.
[b]Determined by $^1$H NMR (CDCl$_3$).
[c]Isolated yield.
[d]Static vacuum (1.10$^{-5}$ bar).

Example 7: Homocoupling of Terminal Olefins in Presence of an Acid as an Additive

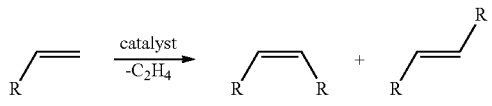

In a glove box, a 3 mL vial equipped with a screw cap and a magnetic stirring bar was charged with the catalyst, phenylphosphoric acid, and the substrate (2 mmol). The vial was closed and the reaction mixture was stirred at room temperature (20° C.).

TABLE 8

Metathesis homocoupling of terminal olefins in presence of an acid (neat substrate)

| entry | catalyst | substrate | cat. loading mol % | PPA[a] loading mol % | time, h | temp., ° C. | % conv.[b] | yield[b] | % Z[b] |
|---|---|---|---|---|---|---|---|---|---|
| 1 | 3a | allyl-benzene | 0.1 | 0.1 | 3 | 20 | 16 | 16 | 18 |
|   |    |               |     |     | 10 |   | 46 | 46 | 18 |
|   |    |               |     |     | 16 |   | 53 | 53 | 18 |
| 2 | 4a | allyl-benzene | 0.1 | 0.1 | 2 | 20 | 7 | 6 | 86 |
|   |    |               |     |     | 10 |   | 41 | 21 | 83 |
|   |    |               |     |     | 16 |   | 59 | 29 | 80 |
| 3 | 4a | methyl undecenoate | 0.1 | 0.1 | 24 | 20 | 7 | 6.5 | 83 |
|   |    |               |     |     | 48 |   | 8.5 | 8 | 82 |

[a]Phenylphosphoric acid.
[b]Determined by $^1$H NMR (CDCl$_3$).

Example 8: Homocoupling of Terminal Olefins in Presence of Air (Neat Substrate)

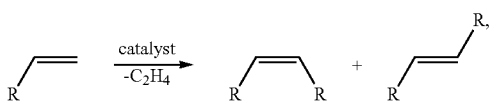

In the fume hood, a 1 mL vial equipped with a septum cap and a magnetic stirring bar was charged with the catalyst, and with 2 mmol of substrate (stored under air). The vial was closed, a syringe needle was inserted through the septum cap, and the reaction mixture was stirred at room temperature (20° C.) or heated in an oil bath.

TABLE 9

Metathesis homocoupling of terminal olefins in presence of air (neat substrate)

| entry | catalyst | substrate | cat. loading mol % | time, h | temp., ° C. | % conv.[a] | yield[a] (isolated)[b] | % Z[a] |
|---|---|---|---|---|---|---|---|---|
| 1 | 3a | allyl-benzene | 0.1 | 3 | 20 | 2.5 | 2.2 | 46 |
|   |    |               |     | 21 |    | 18 | 17.5 | 21 |
| 2 | 4a | allyl-benzene | 0.1 | 3 | 20 | 2 | 2 | 86 |
|   |    |               |     | 21 |    | 15.5 | 15 (15) | 83 |
| 3 | 4a | allyl-benzene | 0.1 | 0.5 | 50 | 5 | 4.5 | 83 |
|   |    |               |     | 2 |    | 15 | 12.5 | 75 |
| 4 | 4a | allyl-benzene | 0.5 | 3 | 20 | 13 | 13 | 86 |
|   |    |               |     | 21 |    | 44 | 40 | 83 |

TABLE 9-continued

Metathesis homocoupling of terminal olefins in presence of air (neat substrate)

| entry | catalyst | substrate | cat. loading mol % | time, h | temp., ° C. | % conv.[a] | yield[a] (isolated)[b] | % Z[a] |
|---|---|---|---|---|---|---|---|---|
| 5 | 4a | allyl-benzene | 0.5 | 1 | 35 | 30 | 22 | 83 |
|   |    |               |     | 2 |    | 43 | 30 | 83 |
|   |    |               |     | 4 |    | 54 | 38 | 81 |
|   |    |               |     | 8 |    | 60 | 42 | 79 |
|   |    |               |     | 18 |   | 72 | 52 | 75 |

[a]Determined by $^1$H NMR (CDCl$_3$).
[b]Isolated yield.

Example 9: Homocoupling of Allylbenzene Using 4a in Presence of Air (in Solution)

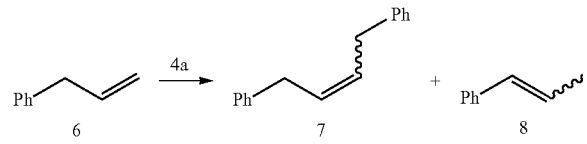

In the fume hood, a 50 mL Schlenk flask equipped with a Young's tap and a magnetic stirring bar was charged with the catalyst (0.005 mmol), and with 2 mmol of substrate (stored under air). The solvent (stored under air) was added to the flask to obtain 0.5 mL of a 4 M solution. The Schlenk flask was closed and the reaction mixture was stirred and heated in an oil bath at 40° C.

TABLE 10

Metathesis homocoupling of allylbenzene using 4a in presence of air (in solution)[a]

| entry | solvent | time, h | % conv.[b] | 7/8[b] | % Z[b] |
|---|---|---|---|---|---|
| 1 | allylbenzene | 2 | 15 | 9.5 | 82 |
|   |              | 4 | 27 | 5.8 | 79 |
|   |              | 8 | 40 | 5.7 | 79 |
|   |              | 12 | 43 | 5.6 | 76 |
| 2 | methyl acetate | 2 | 9 | 8 | 82 |
|   |                | 4 | 16 | 9.3 | 81 |
| 3 | tetrahydrofuran | 2 | 8 | 7 | 86 |
|   |                 | 4 | 13 | 6.9 | 86 |
| 4 | dioxane | 2 | 11 | 9 | 86 |
|   |         | 4 | 15 | 3.8 | 85 |
| 5 | methanol | 2 | 8 | 3 | 85 |
|   |          | 4 | 14 | 2 | 86 |
| 6 | ethanol | 2 | 7 | 20.7 | 82 |
|   |         | 4 | 11 | 14.3 | 81 |
| 7 | Isopropanol | 2 | 8 | 3 | 84 |
|   |             | 4 | 20 | 2.4 | 84 |
| 8 | acetone | 2 | 5 | 3.7 | 79 |
|   |         | 4 | 9 | 4.3 | 75 |
| 9 | toluene | 2 | 10 | 9 | 77 |
|   |         | 4 | 17 | 16 | 69 |
| 10 | fluorobenzene | 2 | 16 | 3 | 67 |
|    |               | 4 | 23 | 6.7 | 58 |
| 11 | CH$_2$Cl$_2$ | 2 | 11 | 4.5 | 73 |
|    |              | 4 | 17 | 7.5 | 64 |

[a]Catalyst loading 0.25 mol %, allylbenzene 2 mmol, Substrate concentration 4M, T = 40° C.
[b]Determined by $^1$H NMR (CDCl$_3$).

Example 10

Preparation of Ruthenium Complex 4b

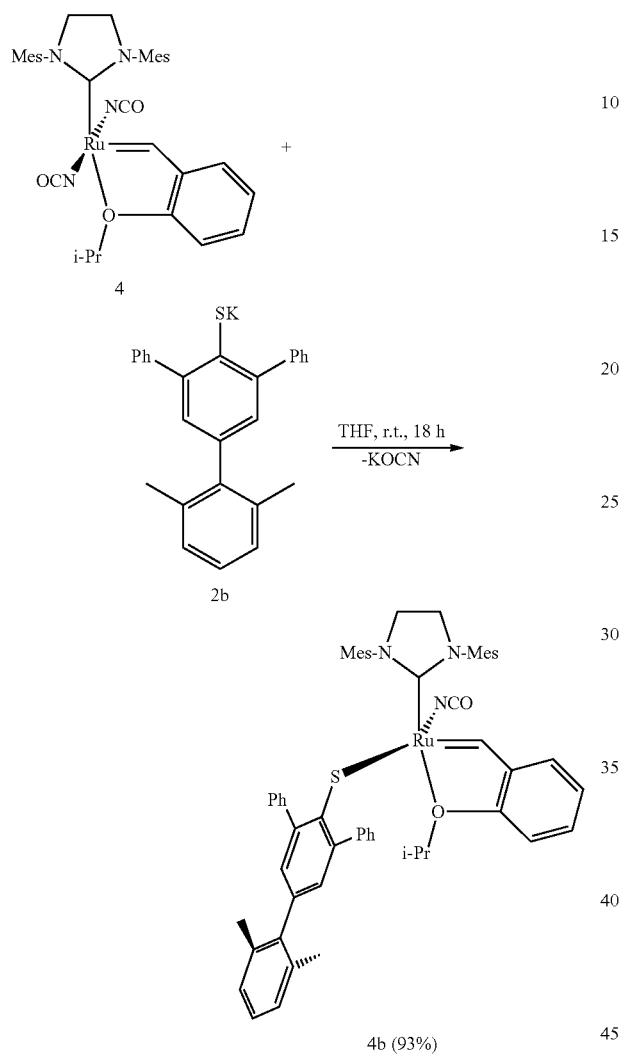

In a glovebox, complex 4 (132 mg, 0.206 mmol) and potassium 2,6-diphenyl-4-(2,6-dimethylphenyl)benzenethiolate (92 mg, 0.226 mmol) 2b were suspended in tetrahydrofuran (2 mL) and the mixture stirred at room temperature for 18 hours. The solvent was removed under reduced pressure and the residue passed through a silica gel column using diethyl ether/hexane (1:1) as eluent, which was then changed in diethyl ether/hexane (7:3), after the green fraction reached half column. The green fraction was collected, the solvent removed under vacuum to give 184 mg (93%) of the title compound 4b. 1H NMR (600.17 MHz, CD$_2$Cl$_2$): δ=14.44 (s, 1H), 7.70-7.79 (br m, 5H), 7.32 (ddd, J=8.3, 7.4, 1.6, 1H), 7.10-6.84 (br m, 6H), 6.78 (td, J=7.4, 0.7, 1H), 6.84-6.60 (br m, 7H), 6.57 (d, J=8.3, 1H), 6.47 (br, 1H), 6.47 (dd, J=7.4, 1.6, 1H), 4.31 (sept, J=6.1 Hz, 1H), 3.92 (s, br, 4H), 2.40 (s, 6H), 2.37 (s, 6H), 2.15 (s, 6H), 2.10 (s, 3H), 1.83 (s, 3H), 0.96 (d, J=6.1 Hz, 3H), 0.70 (d, J=6.1 Hz, 3H). 13C{1H} NMR (150.91 MHz, CD$_2$Cl$_2$): δ=275.34, 275.32, 208.88, 153.35, 148.45, 145.95, 145.28, 144.66, 141.21, 141.12, 140.16, 138.03, 137.98, 137.89, 136.60, 136.36, 135.99, 135.44, 131.64, 130.90, 130.80, 130.34, 129.20, 128.76, 127.80, 127.64, 127.59, 127.26, 127.20, 126.98, 126.69, 126.33, 124.86, 122.51, 121.48, 112.38, 75.68, 51.59, 21.25, 21.19, 20.77, 20.64, 20.51, 18.68, 18.28. HRMS (ESI$^+$), m/z: 985.33014 [M+Na]$^+$; calculated for C$_{58}$H$_{59}$N$_3$NaO$_2$$^{101}$RuS: 985.32815.

Example 11

Preparation of Ruthenium Complex 4c

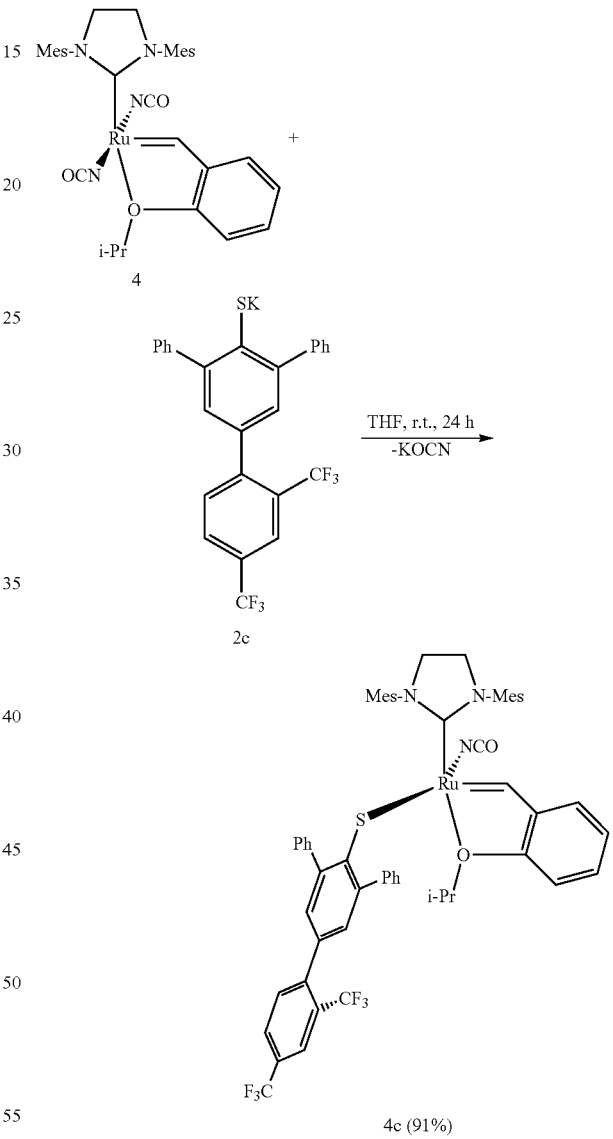

In a glovebox, complex 4 (300 mg, 0.457 mmol) and potassium 2,6-diphenyl-4-(2,4-ditrifluoromethylphenyl)benzenethiolate (258 mg, 0.503 mmol) 2c were suspended in tetrahydrofuran (8 mL) and the mixture stirred at room temperature for 24 hours. The solvent was removed under reduced pressure and the residue passed through a silica gel column using diethyl ether/hexane (7:3) as eluent. The green fraction was collected, the solvent removed under vacuum to give 445 mg (91%) of the title compound 4c. 1H NMR (600.17 MHz, CD2Cl2): δ=14.43 (s, 1H), 7.94 (br s, 1H), 7.71 (br d, J=8.2, 1H), 7.67-7.42 (br m, 5 H), 7.40-7.30 (m, 2H), 6.98 (br s, 2H), 6.94 (br s, 1H), 6.89 (br s, 1H), 6.81 (br dt, J=7.4, 0.6, 1H), 6.79-6.67 (br m, 6H), 6.65 (br s, 1H), 6.60 (br d, J=8.3, 1H), 6.60 (br d, J=8.2, 1H), 6.47 (br dd, J=7.5, 1.5, 1H), 4.28 (sep, J=6.1 Hz, 1H), 3.93 (s, 4H), 2.38 (s, 6H), 2.37 (s, 6H), 2.14 (s, 6H), 0.94 (d, J=6.1, 3 H), 0.65 (d, J=6.1, 3 H). 13C{1H} NMR (150.91 MHz, $CD_2Cl_2$): δ=277.28, 277.26, 209.20, 153.74, 148.58, 146.25, 145.28, 145.22, 145.14, 144.13, 141.10, 138.44, 138.29, 136.29, 134.43, 131.39, 131.26, 131.18, 129.92, 129.64, 129.17, 128.43, 128.40, 128.22, 128.00, 127.06, 125.63, 123.72, 122.91, 121.97, 113.10, 76.11. 51.97, 21.19, 21.06, 20.98, 19.08, 18.68. HRMS (ESI+), m/z: 1093.27547 [M+Na]+; calculated for $C_{58}H_{53}F_6N_3NaO_2{}^{101}RuS$: 1093.27162.

Example 12

Preparation of Ruthenium Complex 16a

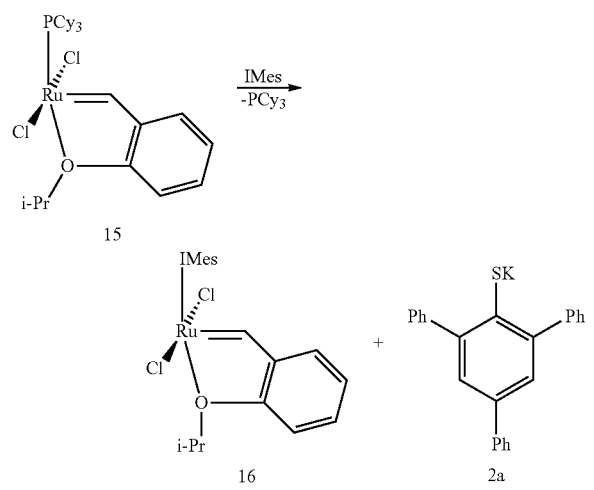

Complex 16 (125 mg, 0.200 mmol, which was prepared from Hoveyda-Grubbs first generation catalyst 15 according to literature procedure (31), was dissolved in THF (4 ml) and potassium 2,4,6-triphenylthiophenolate 2a (78 mg 0.200 mmol) was added as a solid in small portions. Residual reactant was transferred into the reaction mixture as a solution/suspension in THF (1 ml). The mixture was stirred for 4 h before all volatiles were removed under reduced pressure. The solid green residue was extracted with toluene (4×1 ml), and the green solution filtered and dried in vacuum leaving a green solid 208 mg). 1H-NMR showed the presence of toluene that could not be removed in vacuum. Therefore the target compound was treated repeatedly with DCM/pentane followed by drying in vacuum, reducing the mass to 0.185 mg. The residual was dissolved in 0.5 mL $CH_2Cl_2$, and then pentane (10 ml) was slowly added, in such a way as to obtain two separate layers, which were allowed to diffuse slowly (one week) into each other at −32° C. The dark green crystals of 7a.$CH_2Cl_2$.$C_5H_{12}$ were isolated and washed three times with pentane (145 mg, yield=67%). 1H NMR (500.13 MHz, $CD_2Cl_2$): δ=14.47 (s, 1H, Ru=CH), 7.67-7.60 (m, 2H), 7.58-7.51 (m, 2H), 7.44-7.40 (m, 2H), 7.36-7.29 (m, 3H), 7.27-7.21 (m, 1H), 7.17 (br, 1H), 7.05 (t, J=7.2 Hz, 1H), 6.97 (br, 2H), 6.94 (s, 2H), 6.91-6.73 (m, 8H), 6.59 (dd, J=7.6, 1.5 Hz, 1H), 6.50 (d, J=8.3 Hz, 1H), 4.27 (sep, J=6.1 Hz, 1H), 2.42 (s, 6H), 2.15 (s, 6H), 2.04 (s, 6H), 1.07 (d, J=6.1 Hz), 0.66 (d, J=6.1 Hz). 13C{1H} NMR (150.90 MHz, $CD_2Cl_2$): δ=272.40, 176.26, 153.78, 149.54, 147.54, 146.79, 145.14, 142.86, 141.82, 141.13, 138.99, 137.91, 137.49, 137.15, 136.64, 131.23, 130.29, 130.22, 129.65, 129.39, 129.35, 129.28, 129.16, 129.05, 128.99, 128.84, 128.73, 128.58, 128.43, 128.31, 127.89, 127.68, 127.52, 127.43, 127.26, 127.01, 126.89, 125.79, 125.66, 125.23, 122.58, 122.58, 121.94, 113.47, 76.26, 51.98, 21.65, 21.30, 20.92, 19.60, 18.86. HRMS (DART), m/z: 928.26871 [M+H]+, calculated for C55H5437ClN2OS101Ru: 928.26717.

Example 13

Preparation of Ruthenium Complex 17a

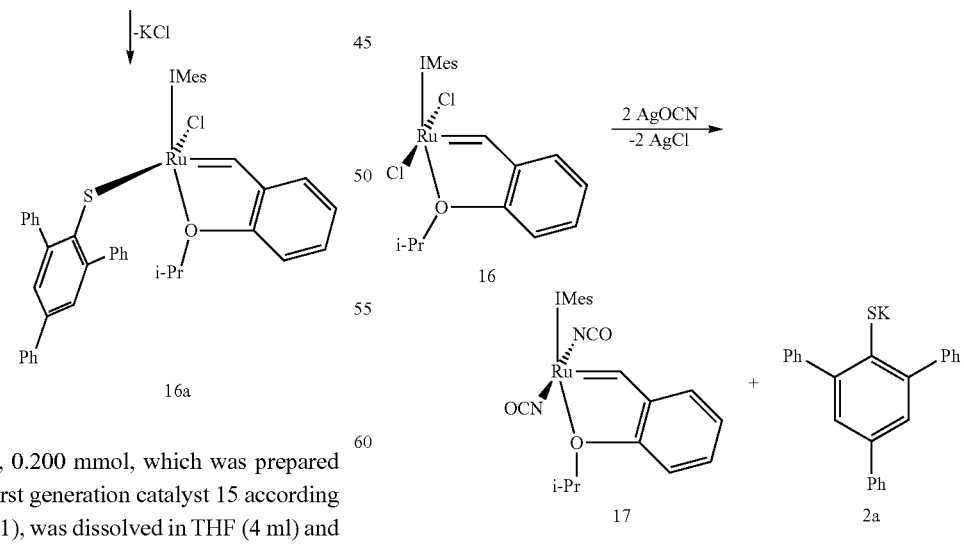

-continued

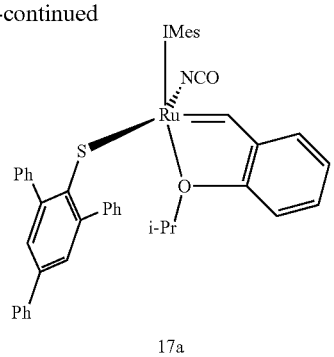

17a

In a glovebox complex 16 (0.125 g, 0.200 mmol) was dissolved in dichloromethane (3 ml), resulting in a dark green solution. AgOCN (149.89 g/mol, 0.460 mmol, 0.0689 g, 2.3 eq.) was suspended in DMF (2 ml) and slowly added. The reaction mixture was stirred for 3.5 h at room temperature before it was filtered and the resulting brown-green solution dried in vacuum. The residual was dissolved in toluene and the resulting solution was filtered and dried in vacuum to give complex 17 as a brown foam (125 mg, yield=98%). 1H NMR (400.13 MHz, $C_6D_6$): δ=16.65 (s, 1H), 7.06 (d, J=7.4, 2 H), 6.86 (s, 4H), 6.67 (t, J=7.4, 1H), 6.22 (d, J=8.3, 1H), 6.12 (s, 2H), 4.25 (sep, J=6.1, 1H), 2.23 (s, 12H), 1.86 (s, 6H), 1.07 (d, J=6.1, 6 H).

Complex 17 was dissolved in THF (5 ml) and 2a (78 mg, 0.200 mmol) was added as a solid in small portions. Residual reactant was transferred into the reaction mixture as a solution/suspension in THF (1.5 ml). After 2 h a dark green solution had formed. The mixture was stirred for another 70 hours before all volatiles were removed under reduced pressure. The residual was dissolved in a minimum amount of dichloromethane, and then pentane was slowly added, in such a way as to obtain two separate layers, which were allowed to diffuse slowly (one week) into each other at −32° C. The dark green crystals of $8a.CH_2Cl_2.C_5H_{12}$ were isolated and washed three times with pentane and dried in the glovebox (82 mg, yield=38%).

1H NMR (600.17 MHz, $CD_2Cl_2$): δ=14.44 (s, 1H, Ru=CH), 7.68-7.59 (br m, 2H), 7.59-7.50 (br m, 3H), 7.46-7.41 (m, 2H), 7.38-7.30 (m, 3H), 7.27-7.21 (m, 1H), 7.18 (br d, J=1.9, 1H), 7.05-6.97 (br m, 3H), 6.95 (s, 2H), 6.90-6.70 (br m, 8H), 6.60 (br dd, J=7.5, 1.5 Hz, 1H), 6.54 (br d, J=8.3, 1H), 4.25 (sep, J=6.1 Hz, 1H), 2.41 (s, 6H), 2.13 (s, 6H), 1.97 (s, 6H), 0.94 (d, J=6.1 Hz), 0.59 (d, J=6.1 Hz). 13C{1H} NMR (150.91 MHz, $CD_2Cl_2$): δ=272.51, 272.48, 175.90, 153.92, 149.22, 147.26, 145.54, 145.17, 142.73, 141.54, 141.03, 139.19, 137.57, 137.30, 137.15, 136.07, 131.70, 131.19, 129.28, 129.05, 128.98, 128.82, 128.56, 128.32, 127.84, 127.72, 127.60, 127.26, 126.98, 126.91, 125.63, 124.96, 122.79, 122.16, 113.11, 76.29, 21.26, 21.07, 20.70, 19.77, 18.51. HRMS (ESI+), m/z: 955.28427 [M+Na]+; calculated for $C_{56}H_{53}N_3NaO_2{}^{101}RuS$: 955.28120.

Example 14

Preparation of Ruthenium Complex 9d

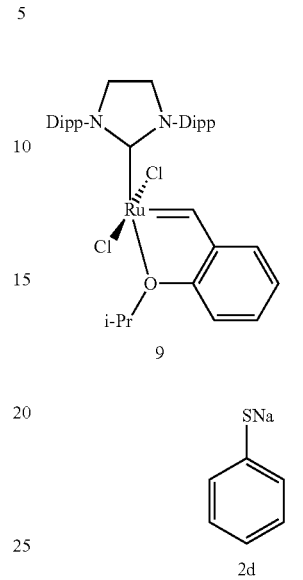

Dipp = 2,6-diisopropylphenyl

In a glovebox, Complex 9 (54 mg, 0.076 mmol) and sodium thiophenolate (12 mg, 0.091 mmol) 2d were suspended in tetrahydrofuran (3 mL) and the mixture stirred at room temperature for 3 hours. Then, an additional amount of 2d (3 mg, 0.023 mmol) was added to the mixture and the mixture was stirred at room temperature for further three hours. The solvent was removed under reduced pressure and the residue was passed through a silica gel column using diethyl ether/hexane (2:8) as eluent. The green-brownish fraction was collected, the solvent removed under vacuum to give 17 mg (yield=29%) of the title compound 9d.

1H NMR (400.13 MHz, $C_DCl_3$): δ=14.69 (s, 1H, Ru=CH), 7.52 (t, J=7.7 Hz, 2H), 7.39 (dd, J=7.7, 1.5 Hz, 2H), 7.34-7.28 (m, 3H), 6.86-6.78 (m, 2H), 6.73 (dt, J=7.4, 1.3 Hz, 1H), 6.59 (t, J=7.7 Hz, 2H), 6.33 (d, J=8.3 Hz, 1H), 6.26 (dd, J=8.3, 1.1 Hz, 2H), 4.30-4.03 (m, 4H), 3.93-3.59 (m, 5H), 1.53-1.36 (br, 6H), 1.32 (d, J=6.9 Hz, 6H), 1.30-1.18 (Br, 6H), 1.23 (d, J=6.9 Hz, 6H), 1.16 (d, J=6.1 Hz, 3H), 1.04 (d, J=6.1 Hz, 3H). HRMS (DART), m/z: 784.28486 [M+H]+, calculated for C43H5635ClN2OS101Ru: 784.28577.

Example 15

Preparation of Ruthenium Complex 10d

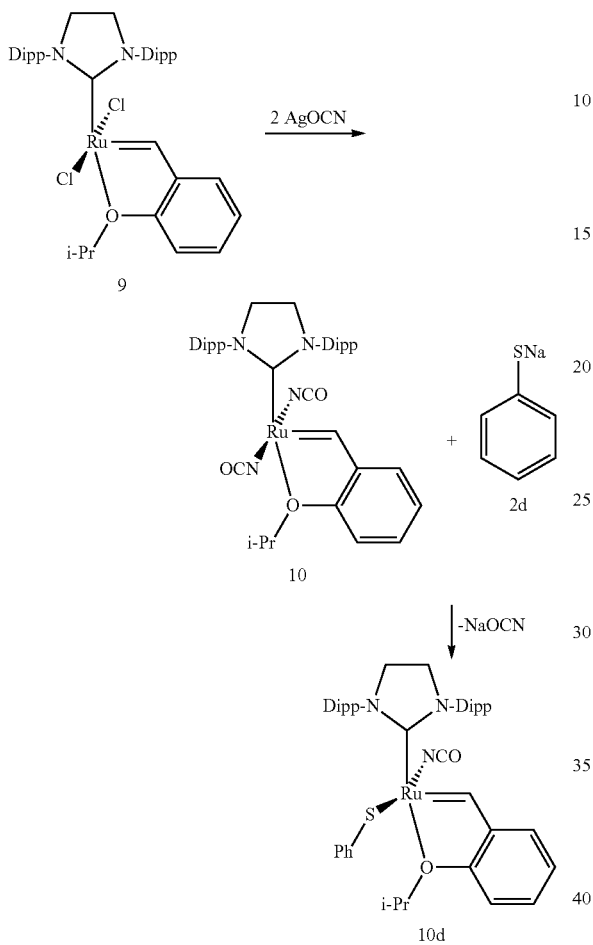

Dipp = 2,6-diisopropylphenyl

In a glovebox 9 (300 mg, 0.42 mmol) were dissolved in 7 ml of dichloromethane, then AgOCN (146 mg, 0.97 mmol) were suspended in 2 ml dimethylformamide and slowly added to the solution of 9. The reaction mixture was stirred for 5 h at room temperature and then the solvent was removed under vacuum. The residual was dissolved in dichloromethane and filtered through a short pad of silica gel using dichloromethane/diethyl ether (9:1) as eluent. The solution was concentrated under vacuum and then pentane was added. The mixture was cooled at −80° C. and the yellow-green precipitated was isolated by cannula filtration and washed two times with pentane. The solid was transferred in the glove box and dried under argon atmosphere until a constant weight was reached to give compound 10 in a yield of 53% (164 mg). 1H NMR (600.17 MHz, CDCl3): δ=16.39 (s, 1H), 7.58 (t, J=7.8, 2 H), 7.54 (ddd, J=8.3, 7.4, 1.6, 1H), 7.42 (d, J=7.7, 4H), 6.92 (dt, J=7.4, 0.7, 1H), 6.87 (d, J=8.3, 1H), 6.85 (dd, J=7.7, 1.6, 1H), 4.88 (sep, J=6.2, 1H), 4.18 (s, 4H), 3.40 (sep, J=6.8, 4 H), 1.28 (d, J=6.9, 12 H), 1.25 (d, J=6.7, 12 H), 1.15 (d, J=6.2, 6 H). 13C{1H} NMR (150.90 MHz, CDCl$_3$): δ=296.38, 212.84, 152.85, 149.45, 143.55, 136.13, 135.22, 130.44, 130.42, 124.95, 123.06, 122.69, 113.04, 75.07, 54.83, 29.47, 26.63, 23.02, 21.17. HRMS (ESI$^+$), m/z: 746.28495 [M+Na]$^+$; calculated for $C_{39}H_{50}N_4NaO_3{}^{101}Ru$: 746.28364.

In a glovebox, 10 (100 mg, 0.138 mmol) was dissolved in 44 ml of tetrahydrofuran and while stirring at room temperature 2d (20.3 mg, 0.154 mmol), dissolved in 16 ml of tetrahydrofuran, was added in 4 equal portions (4×4 ml) with an interval of one hour between every addition. After the last addition the mixture was stirred at room temperature for further three hours. The solvent was removed in vacuo and the dark brown residue was purified by column chromatography on silica gel using diethyl ether/hexane (3:2) as eluent. The volatiles were removed in vacuo and the residue was dissolved in 1 ml of dichloromethane and precipitated with pentane. The suspension was cooled at −80 degrees and the brown solid was isolated by cannula filtration and washed 3 times with cold pentane. The isolated compound was transferred in the glovebox and dried under argon atmosphere (33 mg, yield=30%). 1H NMR (600.17 MHz, CDCl$_3$): δ=14.64 (s, 1H, Ru=CH), 7.53 (t, J=7.7 Hz, 2H), 7.41 (dd, J=7.8, 1.4 Hz, 2H), 7.35 (dd, J=7.8, 1.4 Hz, 2H), 7.33-7.28 (m, 1H), 6.88-6.79 (m, 2H), 6.73 (dt, J=7.2, 1.1 Hz, 1H) 6.57 (t, J=7.7 Hz, 2H), 6.30 (d, J=8.3 Hz, 1H), 6.21 (dd, J=8.3, 1.1 Hz, 2H), 4.29-4.06 (m, 4H), 3.78-3.64 (m, 3H), 3.57 (sep, J=6.8 Hz, 1H), 1.46 (d, J=6.5 Hz, 6H), 1.33 (d, J=6.9 Hz, 6H), 1.24 (d, J=6.9 Hz, 12H) 1.08 (d, J=6.0 Hz, 3H), 0.92 (d, J=6.1 Hz, 3H). 13C{1H} NMR (150.90 MHz, CDCl$_3$): δ=267.25, 213.79, 151.92, 148.97, 148.82, 144.40, 143.49, 137.11, 132.90, 129.74, 127.76, 126.86, 124.50, 124.38, 123.33, 122.83, 122.31, 113.50, 74.09, 54.89, 29.86, 29.24, 29.10, 26.80, 26.73, 23.60, 23.35, 21.63, 20.69. HRMS (ESI$^+$), m/z: 813.29792 [M+Na]$^+$; calculated for $C_{44}H_{55}N_3NaO_2{}^{101}RuS$: 813.29685.

Example 16

Preparation of Ruthenium Complex 12a

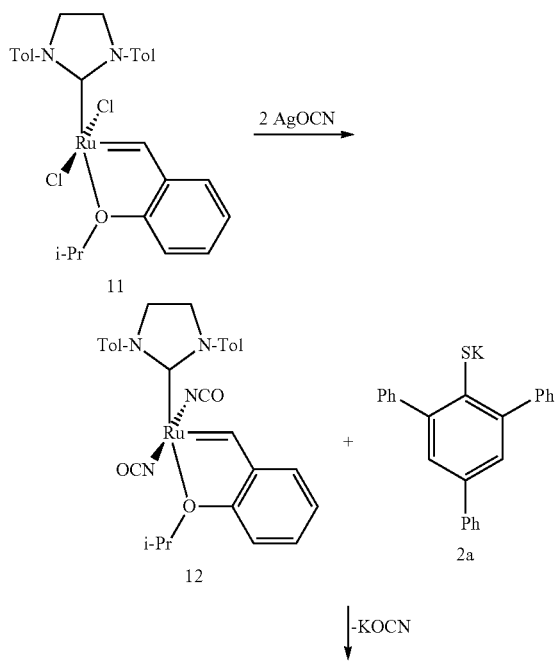

-continued

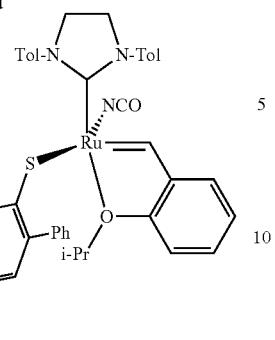

Tol = tolyl

In a glovebox 11 (300 mg, 0.54 mmol) and AgOCN (180 mg, 1.21 mmol) were suspended in 5 ml of tetrahydrofuran. The mixture was stirred for three hours at room temperature, and then the solvent was removed under vacuum. The residual was dissolved in dichloromethane and filtered through a short pad of silica gel using dichloromethane/diethyl ether (9:1) as eluent. The brown solution containing complex 12 was concentrated under vacuum and the compound was precipitated with pentane at room temperature. The brown solid was isolated by cannula filtration and washed three times with pentane. The solid was transferred in a glove box and dried under argon atmosphere (309 mg, 98% of yield). 1H NMR (600.17 MHz, CDCl$_3$): δ=16.42 (br s, 1H), 8.61-7-30 (br m, 9H), 6.89 (br t, J=7.5, 1H), 6.84 (br d, J=8.3, 1H), 6.82-6.75 (br m, 1H), 4.89 (br sep, J=6.1, 1H), 4.52-3.96 (br m, 4H), 2.54 (br s, 6H), 1.33-1.03 (br m, 6H). 13C{1H} NMR (150.91 MHz, CDCl$_3$): δ=, 299.50, 298.27, 210.71, 209.94, 152.87, 142.97, 140.42, 138.02, 137.29, 134.76, 134.43, 132.23, 131.89, 131.67, 130.08, 129.66, 129.25, 129.19, 129.02, 128.11, 127.77, 126.65, 122.11, 121.74, 112.54, 74.34, 52.80, 21.34, 18.10. HRMS (ESI$^+$), m/z: 606.12791 [M+Na]$^+$; calculated for C$_{23}$H$_{30}$N$_4$NaO$_3$$^{101}$Ru: 606.12714.

In a glovebox, 12 (150 mg, 0.26 mmol), and 2a (106 mg, 0.28 mmol) were transferred to a 10 mL vial equipped with a screw cap, followed by addition of 4 mL of THF, and the mixture was stirred at room temperature for 15 hours. The solvent was removed under vacuum, and the residue was purified by column chromatography on silica gel using diethyl ether/hexane (8:2) as eluent. The solvent was removed under vacuum and the residual was further purified by dissolving the solid in a minimum amount of dichloromethane followed by precipitation with pentane at room temperature. The solid was isolated by cannula filtration and washed three times with pentane. The yellow-green solid was transferred in a glove box and dried under argon atmosphere (82 mg, yield 36%). 1H NMR (600.17 MHz, CDCl$_3$): δ=14.45 (br s, 0.2H, Ru=CH), 14.39 (br s, 0.8H, Ru=CH), 8.12-6.54 (br m, 27H), 7.71 (dd, J=8.5, 2.2 Hz, 2H), 77.61-7.44 (m, 5H), 6.50 (br d, J=8.1, 1H), 6.39 (br d, J=6.8, 1H), 4.38 (br sep, J=5.5 Hz, 1H), 4.22-3.80 (br m, 4H), 2.77 (br s, 0.5H), 2.29 (br s, 5.5H), 1.08-077 (br m, 3H), 0.65 (br d, J=5.5 Hz, 2.5H), 0.53 (br s, 0.5H). 13C{1H} NMR (150.91 MHz, CDCl$_3$): δ=276.95, 275.19, 210.78, 209.20, 153.78, 148.42, 147.38, 144.26, 143.32, 142.29, 141.39, 141.33, 140.97, 140.84, 139.95, 137.52, 137.20, 131.98, 131.36, 131.10, 130.23, 129.90, 129.17, 128.78, 128.61, 128.40, 128.01, 127.80, 127.77, 127.41, 127.11, 126.97, 126.84, 125.47, 122.86, 121.78, 112.40, 112.10, 75.06, 54.93, 51.94, 22.16, 21.81, 20.81, 20.16, 18.16, 17.72. HRMS (ESI$^+$), m/z: 901.23813 [M+Na]$^+$; calculated for C$_{52}$H$_{47}$N$_3$NaO$_2$$^{101}$RuS: 901.23425.

Example 17

Preparation of Ruthenium Complex 14b

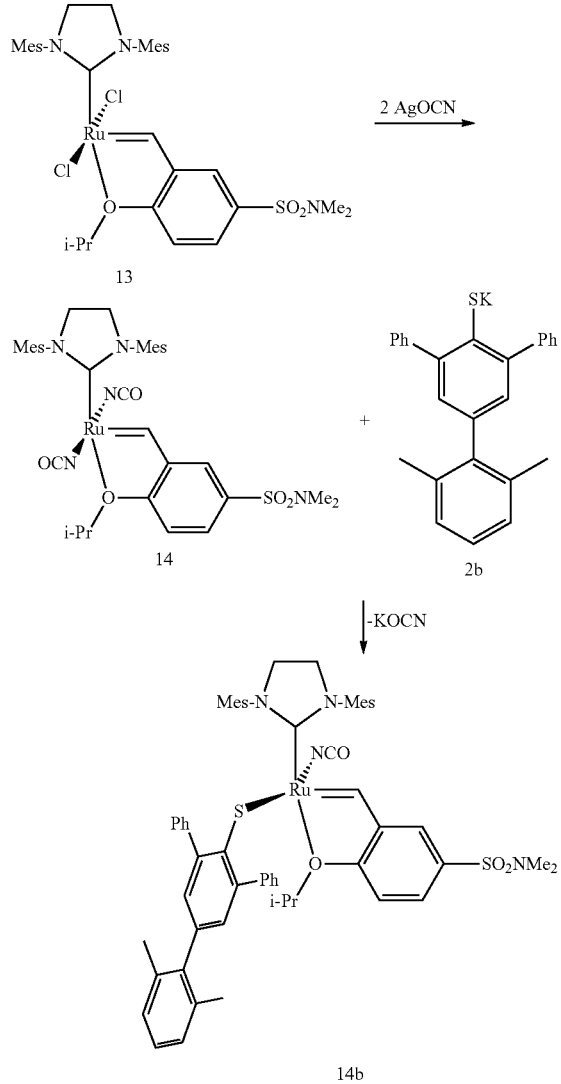

Mes = mesityl
Me = methyl

In a glovebox 13 (800 mg, 1.09 mmol) and AgOCN (374 mg, 2.51 mmol) were suspended in 10 ml of tetrahydrofuran. The mixture was stirred for three hours at room temperature, and then the solvent was removed under vacuum. The residual was dissolved in dichloromethane and filtered through a short pad of silica gel using dichloromethane/diethyl ether (9:1) as eluent. The green solution containing complex 14 was concentrated under vacuum and the compound was precipitated with pentane at room temperature. The green solid was isolated by cannula filtration and washed three times with pentane. The solid was transferred in a glovebox and dried under argon atmosphere (744 mg, 91% of yield). 1H NMR (600.17 MHz, CD$_2$Cl$_2$): δ=16.25

(br s, 1H), 7.95 (dd, J=8.6, 2.2, 1H), 7.24 (d, J=2.2, 1H), 7.14 (br s, 4H), 6.99 (d, J=8.6, 1H), 4.94 (sep, J=6.1, 1H), 4.19 (s, 4H), 2.27 (s, 6H), 2.43 (s, 6H), 2.41 (s, 12H), 1.11 (d, J=6.1, 6 H). 13C{1H} NMR (150.91 MHz, CD$_2$Cl$_2$): δ=295.12, 207.94, 155.24, 143.75, 139.94, 139.26, 135.84, 135.21, 131.02, 129.94, 129.29, 121.57, 113.36, 76.88, 51.86, 38.07, 21.17, 20.78, 18.45. HRMS (ESI$^+$), m/z: 767.19735 [M+Na]$^+$; calculated for C$_{35}$H$_{43}$N$_5$NaO$_5$$^{99}$RuS: 767.19420.

In a glovebox, 14 (200 mg, 0.27 mmol), and 2b (119 mg, 0.30 mmol) were transferred to a 50 mL Schlenk flask, followed by addition of 15 mL of THF, and the mixture was stirred at 40° C. for 20 hours. The solvent was removed under vacuum, and the target compound 14b was isolated by column chromatography on silica gel using diethyl ether/hexane (9:1) as eluent. The solvent was removed under vacuum and the residue was further purified by dissolving the solid in a minimum amount of dichloromethane followed by precipitation with pentane at room temperature. The green solid was isolated by cannula filtration and washed three times with pentane, transferred in the glovebox and dried under argon atmosphere (231 mg, yield 80%). 1H NMR (600.17 MHz, CDCl$_3$): δ=14.14 (s, 1H, Ru=CH), 7.71 (dd, J=8.5, 2.2 Hz, 2H), 77.61-7.44 (br m, 5H), 7.08-6.91 (br m, 6H), 6.76 (d, J=2.2 Hz, 1H) 6.80-6.66 (br m, 6H), 6.63 (br d, J=8.5 Hz, 1H), 6.56 (br s, 1H), 4.38 (sep, J=6.2 Hz, 1H), 3.95 (s, 4H), 2.72 (s, 6H), 2.42 (s, 6H), 2.39 (s, 6H), 2.15 (s, 6H), 2.08 (br s, 3H), 1.83 (br s, 3H), 1.02 (d, J=6.2 Hz, 3H), 0.71 (d, J=6.2 Hz, 3H). 13C{1H} NMR (150.91 MHz, CDCl$_3$): δ=268.96 (d, J=15 Hz), 207.38, 156.11, 148.43, 145.53, 145.14, 144.06, 140.97, 140.64, 139.20, 138.57, 138.03, 137.32, 136.65, 135.92, 135.12, 132.10, 131.78, 130.87, 130.81, 129.63, 129.01, 127.98, 127.70, 127.64, 127.61, 127.24, 127.01, 126.84, 126.58, 125.79, 121.48, 112.46, 51.74, 38.02, 21.56, 21.23, 21.21, 21.07, 19.05, 18.57. HRMS (ESI$^+$), m/z: 1090.33081 [M+Na]$^+$; calculated for C$_{60}$H$_{64}$N$_4$NaO$_2$$^{99}$RuS: 1090.33260.

Example 18

Homocoupling of Terminal Olefins in Air (Neat Substrate)

In the fume hood, a 3 mL vial equipped with a screw cap and a magnetic stirring bar was charged with the catalyst, and with 2 mmol of substrate (stored under air). The vial was closed and the reaction mixture was stirred at room temperature (20° C.). Conversions, yields, and Z-selectivities were determined from analysis of the 1H NMR spectrum. (28)

| entry | sub.[a] | cat. | X | cat load, mol % | time, hours | % conv.[b] | yield[b] | % Z[b] |
|---|---|---|---|---|---|---|---|---|
| 1 | PB | 4b | NCO | 0.1 | 3 | 4 | 4 | 90 |
|   |    |    |     |     | 24 | 18 | 18 | 88 |
| 2 | PB | 4c | NCO | 0.1 | 9 | 9 | 9 | 85 |
| 3 | PB | 16a | Cl | 0.1 | 3 | 3 | 3 | 79 |
|   |    |    |     |     | 15 | 5 | 5 | 70 |
| 4 | PB | 17a | NCO | 0.1 | 3 | 1 | 1 | 87 |
|   |    |    |     |     | 15 | 3 | 3 | 87 |
| 5 | PB | 9d | Cl | 1 | 1 | 33 | 33 | 24 |
|   |    |    |    |   | 4 | 43 | 42 | 21 |
| 6 | PB | 10d | NCO | 1 | 1 | 7 | 5 | 25 |
|   |    |    |     |   | 4 | 8 | 6 | 22 |
| 7 | PB | 12a | NCO | 0.1 | 1 | 0.7 | 0.7 | 68 |
|   |    |    |     |     | 4 | 1.2 | 1.2 | 67 |
| 8 | PB | 14b | NCO | 0.1 | 1 | 2 | 2 | 93 |
|   |    |    |     |     | 4 | 5 | 5 | 91 |
| 9 | AB | 17a | NCO | 1 | 4 | 6 | 4 | 85 |

[a]PB = 4-phenyl-1-butene, AB = allylbenzene.
[b]Determined by $^1$H NMR.

aPB=4-phenyl-1-butene, AB=allylbenzene. b Determined by 1H NMR.

Example 19: Homocoupling of Terminal Olefins in Presence of Air and in THF Solution at 35° C.

In the fume hood, a 3 mL vial equipped with a screw cap and a magnetic stirring bar was charged with the catalyst (0.01 mmol), and with 1 mmol of allylbenzene (stored under air). THF (stored under air) was added to the flask to obtain 0.25 mL of a 4 M solution. The cap was closed and the reaction mixture was stirred and heated in an oil bath at 35° C. Conversions, yields, and Z-selectivities were determined from analysis of the 1H NMR spectrum. (28)

| entry | sub.[a] | cat. | X | time, hours | % conv.[b] | yield[b] | % Z[b] |
|---|---|---|---|---|---|---|---|
| 1 | AOE | 4b | NCO | 3 | 5 | 5 | 82 |
|   |     |    |     | 10 | 8 | 8 | 78 |
| 2 | AOE | 4c | NCO | 3 | 4 | 4 | 83 |
|   |     |    |     | 10 | 8 | 8 | 78 |
| 3 | AOE | 16a | Cl | 3 | 2 | 2 | 48 |
|   |     |     |    | 10 | 4 | 4 | 45 |
| 4 | AOE | 17a | NCO | 3 | 2 | 2 | 75 |
|   |     |     |     | 10 | 6 | 5 | 71 |
| 5 | AOE | 12a | NCO | 3 | 3 | 2 | 76 |
|   |     |     |     | 10 | 3 | 2 | 75 |
| 6 | AOE | 14b | NCO | 3 | 3 | 3 | 80 |
|   |     |     |     | 10 | 6 | 6 | 78 |
| 7 | AB | 16a | Cl | 4 | 12 | 9 | 79 |
| 8 | AB | 17a | NCO | 4 | 6 | 4 | 84 |

[a]AOE = 4-allyloxyethanol, AB = allylbenzene.
[b]Determined by $^1$H NMR.

Example 20: Homocoupling of Terminal Olefins (Neat) in Presence of Phenylphosphoric Acid In a glove box, a 3 mL vial equipped with a screw cap and a magnetic stirring bar was charged with the catalyst, phenylphosphoric acid (equimolar to the catalyst), and the substrate (2 mmol). The vial was closed and the reaction mixture was stirred at room temperature (20° C.). Conversions, yields, and Z-selectivities were determined from analysis of the 1H NMR spectrum. (28)

| entry | sub.[a] | cat. | X | cat load, mol % | time, hours | % conv.[b] | yield[b] | % Z[b] |
|---|---|---|---|---|---|---|---|---|
| 1 | AB | 4b | NCO | 1 | 1 | 31 | 23 | 76 |
|   |    |    |     |   | 4 | 80 | 43 | 68 |
| 2 | AB | 4c | NCO | 0.1 | 7 | 7 | 7 | 88 |
| 3 | AB | 4c | NCO | 1 | 1 | 18 | 16 | 78 |
|   |    |    |     |   | 4 | 55 | 45 | 71 |
| 4 | AB | 7a | Cl | 1 | 4 | 83 | 76 | 24 |
| 5 | AB | 8a | NCO | 1 | 1 | 25 | 21 | 82 |
|   |    |    |     |   | 4 | 54 | 38 | 80 |

-continued

| entry | sub.[a] | cat. | X | cat load, mol % | time, hours | % conv.[b] | yield[b] | % Z[b] |
|---|---|---|---|---|---|---|---|---|
| 6 | AB | 9d | Cl | 0.1 | 1 | 33 | 30 | 22 |
|   |    |    |    |     | 4 | 54 | 43 | 16 |
| 7 | AB | 10d | NCO | 0.1 | 1 | 20 | 2 | 53 |
|   |    |    |    |     | 4 | 98 | 4 | 50 |
| 8 | AB | 12a | NCO | 0.1 | 1 | 3 | 3 | 77 |
|   |    |    |    |     | 4 | 4 | 3 | 77 |
| 9 | AB | 14b | NCO | 0.1 | 1 | 5 | 4 | 88 |
|   |    |    |    |     | 4 | 19 | 12 | 86 |
|   |    |    |    |     | 15 | 73 | 16 | 80 |
| 10 | PB | 4b | NCO | 0.1 | 4 | 15 | 12 | 93 |
| 11 | MU | 4c | NCO | 1 | 24 | 14 | 12 | 76 |

[a]AB = allylbenzene, PB = 4-phenyl-1-butene, MU = methyl undecenoate.
[b]Determined by $^1$H NMR.

Example 21: Homocoupling of Terminal Olefins in THF 4 M and in Argon Atmosphere In a glovebox, a 50 mL Schlenk flask equipped with a Young's tap was charged with the substrate (2.0 mmol) and the catalyst. The solvent (THF) was added to the flask to obtain 0.5 mL of a 4 M solution, and the reaction mixture was stirred and heated in an oil bath. Determination of conversions, yields, and Z-selectivities were done according to literature procedures. (28)

| entry | sub.[a] | cat. | cat load, mol % | temp., ° C. | time, hours | % conv.[b] | yield[b] (isolated)[c] | % Z[b] |
|---|---|---|---|---|---|---|---|---|
| 1[d] | ATMS | 4b | 0.25 | 60 | 14 | 21 | 16 | 97 |
| 2 | ATMS | 4b | 0.25 | 40 | 24 | 13 | 9 | >97 |
| 3[d] | ATMS | 4c | 0.25 | 60 | 4 | 10 | 8 | 93 |
| 4 | AB | 4b | 0.25 | 40 | 0.5 | 38 | 9 | 87 |
| 5 | AB | 16a | 0.25 | 40 | 0.5 | 8 | 3 | 75 |
|   |    |    |      |    | 2 | 43 | 10 (10) | 50 |
| 6 | PB | 4b | 0.25 | 40 | 1 | 25 | 18 (18) | 93 |

[a]Substrate: allyl trimethylsilane (ATMS), allybenzene (AB), PB = 4-phenyl-1-butene.
[b]Determined by $^1$H NMR.
[c]Isolated yield.
[d]Additive: 1,8-bis(dimethylamino)naphthalene (0.12 mol %).

Example 22: Homocoupling of Terminal Olefins (Neat) in Argon Atmosphere

In a glovebox, a 50 mL Schlenk flask equipped with a Young's tap was charged with the catalyst and the substrate (6.4 mmol). The reaction mixture was stirred and heated in an oil bath (entries 1-4), or stirred at room temperature (entries 5-9). Determination of conversions, yields, and Z-selectivities were done according to literature procedures. (28)

| entry | substrate | cat. | cat load, mol % | temp., ° C. | time, hours | % conv.[a] | Yield[a] (isolated)[b] | % Z[a] |
|---|---|---|---|---|---|---|---|---|
| 1 | 1-octene | 4b | 0.01 | 60 | 1.5 | 9 | 6 (4.5) | 93 |
| 2 | 1-octene | 4c | 0.01 | 60 | 1.5 | 11 | 10 | 91 |
| 3 | 1-octene | 4c | 0.01 | 35 | 24 | 10 | 9 | 85 |
| 4[c] | 1-octene | 16a | 0.01 | 60 | 4 | 18 | 17 | 82 |
| 5 | allyl-benzene | 16a | 0.25 | 20 | 2 | 26 | 16 | 79 |
| 6 | allyl-benzene | 9d | 0.25 | 20 | 0.5 | 48 | 5 (5) | 40 |
| 7 | 4-phenyl-1-butene | 16a | 0.25 | 20 | 2 | 27 | 25 | 86 |
| 8 | allyl-acetate | 16a | 0.25 | 20 | 4 | 15 | 15 | 63 |
| 9 | allyl-acetate | 9d | 0.25 | 20 | 4 | 15 | 15 | 36 |
|   |              |    |      |    | 26 | 31 | 31 | 30 |

[a]Determined by $^1$H NMR.
[b]Isolated yield.
[c]Static vacuum (1 × 10$^{-5}$ bar)

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

REFERENCE (1) Hoveyda, A. H.; Zhugralin, A. R., Nature 2007, 450, 243;
(2) Grubbs, R. H., Adv. Synth. Catal. 2007, 349, 23 and 34;
(3) Thayer, A. M., Chem. Eng. News 2007, 85, 37;
(4) Fürstner, A.; Mathes, C.; Lehmann, C. W., Chem. Eur. J. 2001, 7, 5299;
(5) Gradillas, A.; Perez-Castells, J., Angew. Chem. Int. Ed. 2006, 45, 8086;
(6) Fürstner, A.; Langemann, K., Synthesis-Stuttgart 1997, 792;
(7) Fürstner, A.; Guth, O.; Rumbo, A; Seidel, G., J. Am. Chem. Soc. 1999, 121, 11108;
(8) Jakubec, P.; Cockfield, D. M.; Dixon, D. J., J. Am. Chem. Soc. 2009, 131, 16632;
(9) Trnka, T. M.; Grubbs, R. H., Acc. Chem. Res. 2001, 34, 18;
(10) Lee, C. W.; Grubbs, R. H., Org. Lett. 2000, 2, 2145;
(11) Malcolmson, S. J.; Meek, S. J.; Sattely, E. S.; Schrock, R. R.; Hoveyda, A. H., Nature 2008, 456, 933;
(12) Ibrahem, I.; Yu, M.; Schrock, R. R.; Hoveyda, A. H., J. Am. Chem. Soc. 2009, 131, 3844;
(13) Flook, M. M.; Jiang, A. J.; Schrock, R. R.; Muller, P.; Hoveyda, A. H., J. Am. Chem. Soc. 2009, 131, 7962;
(14) Peryshkov, D. V.; Schrock, R. R.; Takase, M. K.; Müller, P.; Hoveyda, A. H. J. Am. Chem. Soc. 2011, 133, 20754.
(15) Jiang, A. J.; Zhao, Y.; Schrock, R. R.; Hoveyda, A. H., J. Am. Chem. Soc. 2009, 131, 16630;
(16) Meek, S. J.; O'Brien, R. V.; Llaveria, J.; Schrock, R. R.; Hoveyda, A. H. Nature 2011, 471, 461.
(17) Yu, M.; Wang, C.; Kyle, A. F.; Jakubec, P.; Darren J. Dixon, D. J.; Schrock, R. R.; Hoveyda, A. H. Nature 2011, 479, 88.
(18) Wang, C.; Haeffner, F.; Schrock, R. R.; Hoveyda, A. H. Angew. Chem. Int. Ed. 2013, 52, 1939.

(19) Endo, K.; Grubbs, R. H. J. Am. Chem. Soc. 2011, 133, 8525.
(20) Keitz, B. K.; Endo, K.; Herbert, M. B.; Grubbs, R. H. J. Am. Chem. Soc. 2011, 133, 9686.
(21) Keitz, B. K.; Endo, K.; Patel, P. R.; Herbert, M. B.; Grubbs, R. H. J. Am. Chem. Soc. 2012, 134, 693.
(22) Keitz, B. K.; Fedorov, A.; Grubbs, R. H. J. Am. Chem. Soc. 2012, 134, 2040.
(23) Rosebrugh, L. E.; Marx, V. M.; Keitz, B. K.; Grubbs, R. H. J. Am. Chem. Soc. 2013, 135, 10032.
(24) Marx, V. M.; Herbert, M. B.; Keitz, B. K.; Grubbs, R. H. J. Am. Chem. Soc. 2013, 135, 94.
(25) Rosebrugh, L. E.; Herbert, M. B.; Marx, V. M.; Keitz, B. K.; Grubbs, R. H. J. Am. Chem. Soc. 2013, 135, 1276.
(26) Hartung, J.; Grubbs, R. H. J. Am. Chem. Soc., doi: 10.1021/ja4046422.
(27) Jensen, V. R.; Occhipinti, G.; Hansen, F. Novel Olefin Metathesis Catalysts. Int. Patent Appl. WO 2012032131, 2012.
(28) Occhipinti, G.; Hansen, F.; Tornroos, K. W.; Jensen, V. R. J. Am. Chem. Soc., 2013, 135, 3331.
(29) R. Kashif M. Khan, R. K. M.; Torker, S.; Hoveyda, A. H. J. Am. Chem. Soc., doi: 10.1021/ja404208a.
(30) Kumar, P. S.; Wurst, K.; Buchmeiser, M. R. Chem. Asian J. 2009, 4, 1275.
(31) Merino, E.; Poli, E.; Díaz, U.; Brunel, D. Dalton Trans., 2012, 41, 10913-10918.
(32) Occhipinti, G.; Koudriavtsev, V.; Törnroos, K. W., Jensen, V. R. Dalton Trans., 2014, 43, 11106-11117.

The invention claimed is:
1. A compound of Formula (C), (D), (E), or (F):

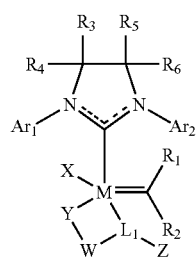 (C)

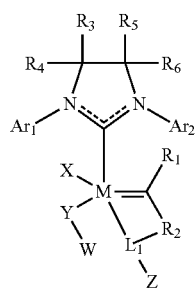 (D)

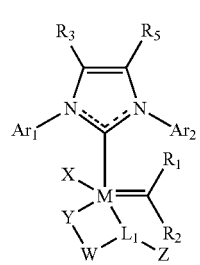 (E)

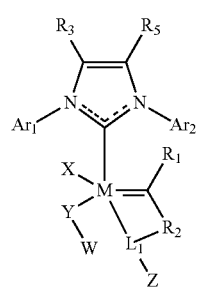 (F)

wherein
each $R_3$, $R_4$, $R_5$, and $R_6$ is independently selected from the group consisting of H, $CF_3$, $NO_2$, halo, CN, —C(O)—R, —C(O)OR, optionally substituted alkyl, optionally substituted aryl, or optionally substituted heteroaryl;
$Ar_1$ and $Ar_2$ are each independently optionally substituted aryl;
M is ruthenium or osmium;
X is selected from the group consisting of —CN, —$N_3$, —NCO, —CNO, —NCS, and —NCSe;
Y is S, Se, or Te;
W is aryl (preferably phenyl), heteroaryl, alkyl, cycloalkyl, or heterocyclyl, wherein the aryl, alkyl, heteroaryl, cycloalkyl, or heterocyclyl is optionally substituted with 1-5 independent $CF_3$, $NO_2$, halo, CN, —C(O)—R, —C(O)OR, alkyl, optionally substituted aryl, or optionally substituted heteroaryl;
R is optionally substituted alkyl, optionally substituted alkenyl, optionally substituted alkynyl, optionally substituted heterocyclyl, optionally substituted cycloalkyl, optionally substituted aryl, or optionally substituted heteroaryl;
each $L_1$ is independently halo, N, S, or O;
each Z is independently absent or alkyl, aryl, or heteroaryl; and
each $R_1$ and $R_2$ are independently hydrogen, optionally substituted alkyl, optionally substituted alkenyl, optionally substituted alkynyl, optionally substituted heterocyclyl, optionally substituted cycloalkyl, optionally substituted aryl, optionally substituted heteroaryl, or $R_1$ and $R_2$ taken together with the carbon atom to which they are attached form an optionally substituted cycloalkyl, optionally substituted heterocyclyl, optionally substituted aryl, or optionally substituted heteroaryl.

2. The compound of claim 1, wherein W is phenyl optionally substituted with 1-5 independent $CF_3$, $NO_2$, halo, CN, —C(O)—R, —C(O)OR, alkyl, optionally substituted aryl, or optionally substituted heteroaryl.

3. The compound of claim 2, wherein W is phenyl substituted with 1-3 independent alkyl.

4. The compound of claim 2, wherein W is phenyl substituted with 1-3 independent aryl.

5. The compound of claim 2, wherein W is (2,4,6-triphenyl)phenyl.

6. The compound of claim 1, wherein Y is S.

7. The compound of claim 1, wherein Y is S and W is phenyl substituted with 1-3 independent aryl.

8. The compound of claim 1, wherein Y is S and W is (2,4,6-triphenyl)phenyl.

9. The compound of claim 1, wherein $Ar_1$ and $Ar_2$ are each independently substituted phenyl.

10. The compound of claim 9, wherein $Ar_1$ is mesityl.

11. The compound of claim 9, wherein $Ar_1$ and $Ar_2$ are mesityl.

12. The compound of claim 1, wherein $Ar_1$ and $Ar_2$ are mesityl; Y is S; and W is (2,4,6-triphenyl)phenyl.

13. The compound of claim 1, wherein X is —NCO or —NCS.

14. The compound of claim 13, wherein M is Ru and X is —NCO or —NCS.

15. The compound of claim 1, wherein Z is isopropyl.

16. The compound of claim 1, wherein the compound is one of compounds 4a and 5a;

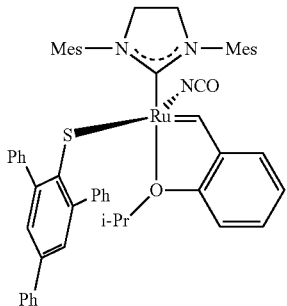

4a

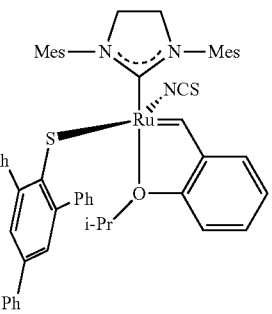

5a

17. A catalyst composition for catalysing olefin metathesis reactions comprising a compound of claim 1.

18. A method of catalysing an olefin metathesis reaction comprising introducing a compound of claim 1 in a reaction medium comprising an olefin.

* * * * *